US008644944B2

(12) United States Patent
Capcelea et al.

(10) Patent No.: US 8,644,944 B2
(45) Date of Patent: Feb. 4, 2014

(54) IMPLANT STIMULATION DEVICE

(75) Inventors: Edmond Capcelea, Sydney (AU);
James F. Patrick, Roseville (AU);
Kostas Tsampazis, North Ryde (AU);
Paul Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/388,937

(22) PCT Filed: Aug. 3, 2010

(86) PCT No.: PCT/AU2010/014909
§ 371 (c)(1),
(2), (4) Date: Feb. 22, 2012

(87) PCT Pub. No.: WO2011/014909
PCT Pub. Date: Feb. 10, 2011

(65) Prior Publication Data
US 2012/0143284 A1    Jun. 7, 2012

(30) Foreign Application Priority Data

Aug. 3, 2009 (AU) ................................. 2009903592
Jan. 14, 2010 (AU) ................................. 2010900128

(51) Int. Cl.
*A61N 1/00* (2006.01)
(52) U.S. Cl.
USPC .......................................................... 607/57
(58) Field of Classification Search
USPC .......................................................... 607/57
See application file for complete search history.

(56) References Cited

U.S. PATENT DOCUMENTS

| 4,592,359 | A | * | 6/1986 | Galbraith ................... 607/57 |
| 6,157,861 | A | | 12/2000 | Faltys et al. |
| 6,249,704 | B1 | | 6/2001 | Maltan et al. |
| 6,393,325 | B1 | | 5/2002 | Mann et al. |
| 6,600,955 | B1 | * | 7/2003 | Zierhofer ................... 607/57 |
| 7,496,405 | B1 | | 2/2009 | Litvak et al. |
| 2004/0082985 | A1 | | 4/2004 | Faltys et al. |
| 2005/0203590 | A1 | | 9/2005 | Zierhofer |
| 2006/0247735 | A1 | | 11/2006 | Honert |

FOREIGN PATENT DOCUMENTS

| WO | 2002/009808 | 2/2002 |
| WO | 2004/043537 | 5/2004 |

OTHER PUBLICATIONS

Macherey, O. et al., "Asymmetric Pulses in Cochlear Implants: Effects of Pulse Shape, Polarity, and Rate", Journal of the Association for Research in Otolaryngology, (2006) vol. 7, pp. 253-266.
International Search Report, International Application No. PCT/AU2010/000976, mailed Oct. 12, 2010 (5 pages).
Written Opinion, International Application No. PCT/AU2010/000976, mailed Oct. 12, 2010 (4 pages).
Extended European Search Report for European Patent Application No. 10805874.4 mailed Jan. 7, 2013 (7 pages).

* cited by examiner

*Primary Examiner* — Christopher D Koharski
*Assistant Examiner* — Nadia Ahmad
(74) *Attorney, Agent, or Firm* — Kilpatrick, Townsend & Stockton, LLP.

(57) ABSTRACT

An implantable stimulation device is disclosed which provides for reduced power consumption when compared with bipolar stimulation and better stimulation performance when compared with monopolar stimulation. Implantable stimulator devices use less power in monopolar stimulation mode than that of bipolar stimulation but stimulation performance is greater when using bipolar stimulation. The device comprises circuitry capable of simultaneous stimulation between a reference electrode and an electrode of a stimulation array and between electrodes of the stimulation array, the ratio of current to the reference electrode and array electrodes being selectable.

20 Claims, 18 Drawing Sheets

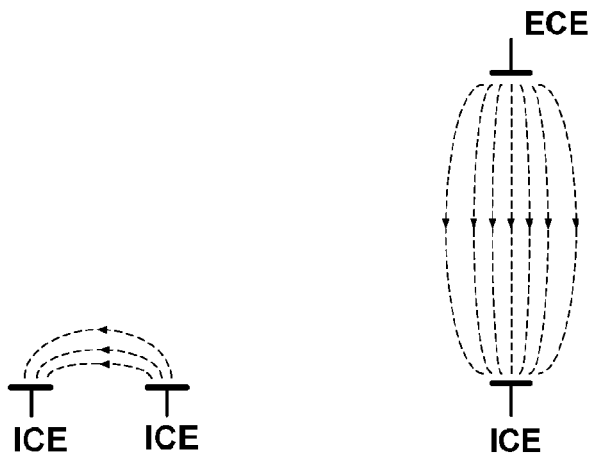
Figure 1
PRIOR ART
Figure 2
PRIOR ART
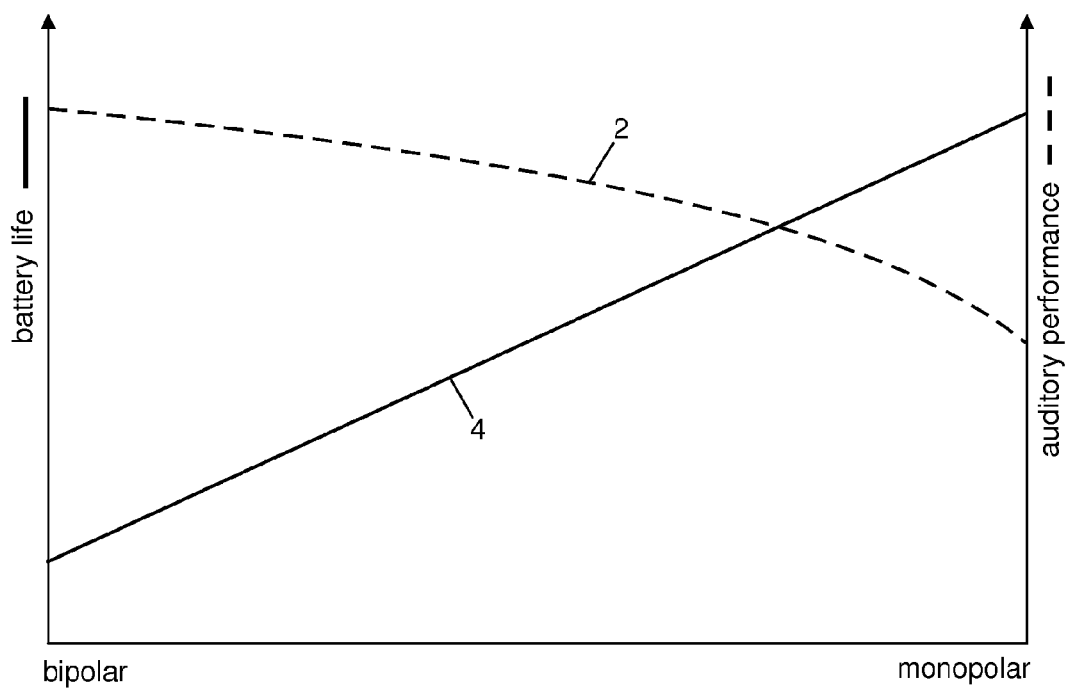
Figure 3

IMPLANT STIMULATION DEVICE

CROSS-REFERENCE TO RELATED APPLICATIONS

This application is a national stage application of PCT Application No. PCT/AU2010/000976, entitled, "Implant Stimulation Device," filed on Aug. 3, 2010, which claims priority from Australian Patent Application No. 2009903592, filed Aug. 3, 2009 and Australian Patent Application No. 2010900128, filed Jan. 14, 2010, which is hereby incorporated by reference herein.

BACKGROUD

1. Field of Invention

The present invention relates to an implantable stimulation device and a method of stimulation for such implants.

2. Related Art

Implantable stimulation devices help to provide nerve stimulation which is inadequate naturally. For example, an implantable hearing device, such as a cochlear implant, has an array of electrodes positioned in the cochlea to provide hearing stimulation. An implantable vestibular device has an array or arrays of electrodes in the vestibular array to provide balance stimulation.

Electrical stimulation is discussed below in relation to a cochlear implant but is equally applicable to other implantable stimulation devices.

In cochlear implants the arrays used in presently available devices typically have tens of electrodes, and the selection of electrodes, currents and timing is controlled in order to induce the desired hearing precepts.

Conventional cochlear implants use two different types of stimulation: intra-cochlear stimulation (between intra-cochlear electrodes (ICEs), being an array of stimulation electrodes), also known as bipolar stimulation, or extra-cochlear stimulation (between an ICE and an extra-cochlear electrode (ECE) or reference electrode), also known as monopolar stimulation.

During intra-cochlear stimulation a current flow between two ICEs stimulates the neural structures located between the two ICEs. The current level must be above the threshold level in order to stimulate the neurons, so as to result in a sensation of hearing for the recipient.

The neurons located in the area of the cochlea between the selected ICEs are stimulated when current flows between the ICEs. All hearing neurons located between the two ICEs are stimulated more or less simultaneously in this mode.

A simplified one-dimensional diagram of the current distribution for intra-cochlear stimulation is depicted in FIG. 1. It can be seen that there are multiple paths for current, the sum of which is the current delivered by the current source. This diagram assumes a relatively homogeneous electrode environment.

FIG. 2 illustrates in simplified form the mechanism of extra-cochlear stimulation. In this mode, current flows between an ICE and an ECE. The hearing neurons located in the area along the current path between the ICE and ECE are stimulated.

US2005/0203590 discloses simultaneous monopolar stimulation, that is, simultaneous stimulation between an extra-cochlear electrode and two intra-cochlear electrodes, of a cochlear implant giving lower power consumption than sequential monopolar stimulation.

SUMMARY

In a first aspect of the present invention, an implantable stimulator device is disclosed. The implantable stimulator device includes: at least one reference electrode, an array of stimulation electrodes, at least one current source; and at least one current control circuit configured to control, the at least one current source to supply a first proportion of a stimulation current to a reference stimulation circuit between the at least one reference electrode and one or more first stimulation electrodes in the array, and to supply a second pre-defined proportion of the stimulation current to an array stimulation circuit between one or more second stimulation electrodes in the electrode array and the one or more first stimulation electrodes.

In a second aspect of the present invention, a method for providing electrical stimulation in an implant, the implant including at least one reference electrode, an array of stimulation electrodes, at least one current source, at least one current control circuit is disclosed. The method comprises: controlling the at least one current source to deliver a first pre-defined proportion of a pre-defined stimulation current to a reference stimulation circuit between the at least one reference electrode and one or more first stimulation electrodes in the array; controlling the at least one current source to deliver a second predefined proportion of a pre-defined stimulation current to an array stimulation circuit between one or more second stimulation electrodes in the electrode array and the one or more first stimulation electrodes.

BRIEF DESCRIPTION OF THE DRAWINGS

Illustrative embodiments of the present invention will be described with reference to the accompanying figures, in which:

FIG. 1 is a schematic illustration of prior art intra-cochlear stimulation;

FIG. 2 is a schematic illustration of prior art extra-cochlear stimulation;

FIG. 3 illustrates the relationship between intra-cochlear stimulation, extra-cochlear stimulation, battery life and auditory performance;

DETAILED DESCRIPTION

Figure 4:
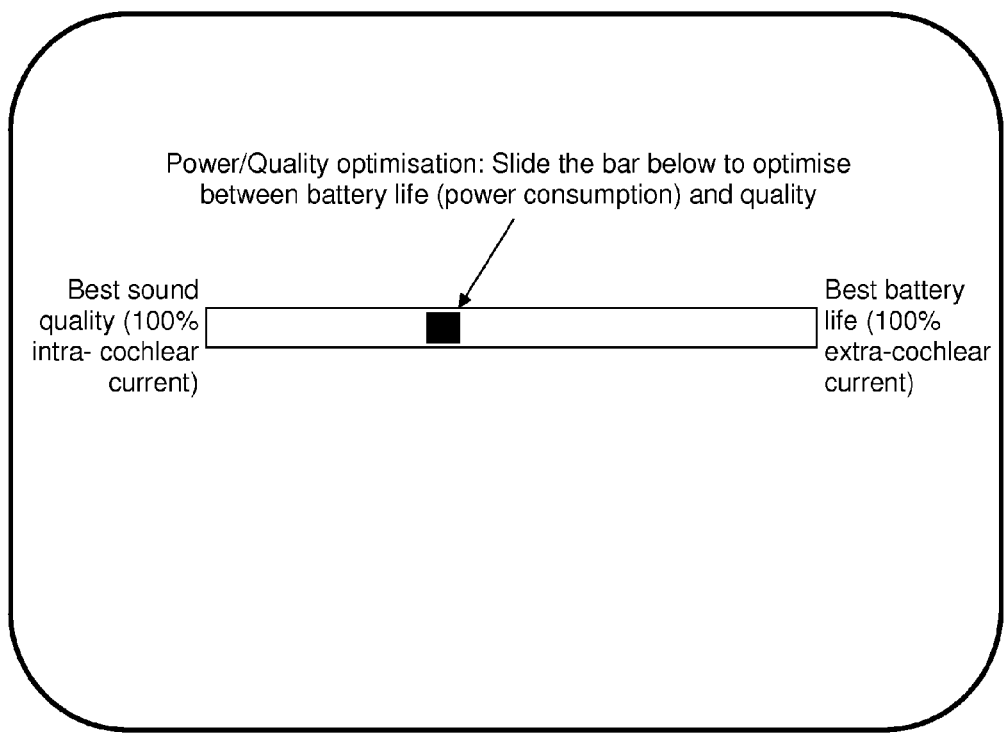
FIG. 4 is a schematic illustration of a user interface used to control the optimization between battery life (power consumption) and sound quality.

Broadly, the present invention provides an implantable stimulation device which provides for reduced power consumption when compared with bipolar stimulation and better stimulation performance when compared with monopolar stimulation.

An implantable stimulator device uses less power in monopolar stimulation mode than that of bipolar stimulation but stimulation or auditory performance, as defined by the ability to localize stimulation to a defined population of nerves, is greater when using bipolar stimulation. The embodiment of an implantable stimulation device disclosed herein provides circuitry capable of simultaneous stimulation between a reference electrode and an electrode of a stimulation array (extra-cochlear stimulation), in a reference stimulation circuit, and between electrodes of the stimulation array (intra-cochlear stimulation), in an array stimulation circuit, by providing a first proportion of a stimulation current in the reference stimulation circuit and a second proportion of the stimulation current in the array stimulation circuit.

Current sources can supply a stimulation current, with the proportion of stimulation current to the reference stimulation circuit or array stimulation circuit being controlled by resistive circuitry, or preferably, variable resistive circuitry, or the current sources can be controlled to deliver the proportion of stimulation current to the reference stimulation circuit or array stimulation circuit directly.

Biphasic stimulation or triphasic stimulation can be provided to provide charge balance.

One embodiment provides for stimulation as described above using a single current source and an alternative embodiment uses multiple current sources.

The implantable stimulation device could be an implantable hearing device, such as a cochlear implantable device, or, for example, a vestibular stimulation device.

An implantable stimulation device and methodology intended for use in a cochlear implant electrical stimulation system is described below. However, the stimulation circuits and methods can be applied to any system in which electrical stimulation is provided, for example a hybrid electrical and acoustic stimulation system, a vestibular stimulation system, or a brain stem or other neural stimulation system. The stimulation circuits and methods can be applied to a system with some implanted components and some external components, or to a fully implanted system. It will be appreciated that the examples are described for illustrative purposes, and the features disclosed are not intended to be limiting.

The embodiments described below are concerned with the electrical stimulation part of the implant system. Those skilled in the art will be familiar with the acoustic processing, signal processing, power supply, data communications, implant configuration and signal processing which are widely employed in existing devices. The embodiments described can be implemented in conjunction with any of these known structures, or any other such structures, and they will accordingly not be discussed in detail. Similarly, the embodiments described can be implemented using electrodes and electrode arrays which are conventional, or with any other suitable electrical stimulus delivery structures.

Cochlear implants with a single current source can use two different types of stimulation: intra-cochlear stimulation (between two ICEs) or extra-cochlear stimulation (between an ICE and an ECE).

FIG. 1 illustrates in simplified form the current flow which is induced during intra-cochlear stimulation. The current stimulates the hearing neurons (cells) located between the ICEs, provided that the current is sufficiently large to exceed the threshold value, and thereby results in a hearing percept. Some hearing neurons located between the two ICEs are stimulated.

FIG. 2 illustrates in simplified form the mechanism of extra-cochlear stimulation. In this mode, current flows between an ICE and an ECE. Some hearing neurons located in the current path between the ICE and ECE are stimulated.

In general, extra-cochlear stimulation uses less power than intra-cochlear stimulation. However, extra-cochlear stimulation can induce undesirable facial nerve stimulation and other unwanted side-effects. In addition, intra-cochlear stimulation can potentially deliver better auditory performance, especially when used with methods such as focused intra-cochlear stimulation, as disclosed in WO2006/119069 and in "Focused intra-cochlear electric stimulation with phased array channels", van den Honert C., Kelsall D., J. Acoustic. Soc. Am, June 2007, 3703-3716.

According to one embodiment, simultaneous intra-cochlear and extra-cochlear stimulation is provided, using a structure to be described below. By delivering both intra-cochlear and extra-cochlear stimulation simultaneously, two varying functions of auditory performance and minimizing power consumption can be optimized against each other. Referring to FIG. 3, a graph of battery life, being a representation of the opposite of power consumption, and auditory performance, going from the extremes of only bipolar (intra-cochlear) stimulation on the left side of the graph to only monopolar (extra-cochlear) stimulation on the right side of the graph, with gradual split of current flow in between, is shown. So, for example, the middle of the graph would represent 50% of current flow by extra-cochlear stimulation and 50% by bipolar stimulation. Auditory performance 2 can be seen to be highest when intra-cochlear stimulation only is used but battery life 4 is lowest at this point. By selecting the amount of intra-cochlear stimulation simultaneously with extra-cochlear stimulation, a desired auditory performance level can be achieved based on, for example, the desired operating time between charges or battery replacement.

It will be appreciated that there are situations which arise when fitting a recipient with a cochlear implant where a useful trade-off can be made by selecting a suitable ratio of intra-cochlear current to extra-cochlear current. In general, stimulation with purely extra-cochlear current (i.e. monopolar stimulation) has the advantage that it requires less stimulation current, less power and results in longer battery life. It has the disadvantage that it is more likely to cause facial nerve stimulation and cause broader spread of excitation of the auditory nerve, meaning the quality of sound delivered to the recipient is poorer. Stimulation with purely intra-cochlear current has the advantage that it produces more focused stimulation, providing the possibility of better quality sound for the recipient. It is also less likely to cause facial nerve stimulation or other side effects of current flow outside the cochlea. It has the disadvantage that it requires more stimulation current and more power and therefore shortens battery life. The embodiments described herein include the provision of a means to vary the ratio of intra-cochlear to extra-cochlear current via, for example, software, a user interface, which optimally could be controlled, for example, by a clinician in the processes of fitting the aforementioned recipient. By varying the ratio of intra-cochlear to extra-cochlear current in the clinical setting it will be possible to select a ratio that gives the optimal performance for each recipient.

For example, a particular recipient has a battery life of 14 hours if purely intra-cochlear stimulation is employed. By mixing in a small fraction of extra-cochlear current in to the stimulation it is possible to extend the battery life to, for example, 16 hours or a full waking day of life. This can be done with only a small broadening of the spread of neural excitation and hence only a small compromise in sound quality. Another recipient prefers to have a much larger fraction of extra-cochlear current used for stimulation, leading perhaps to a 72 hour battery life, at the expense of poorer sound quality. Advantageously, the feature is that the fraction of extra-cochlear to intra-cochlear current is under external control and can be adjusted at the time of fitting a recipient. In current fitting sessions this parameter is fixed (i.e. stimulus with only purely intra-cochlear or purely extra-cochlear current can be selected—not a mixture of the two).

In another example a clinician can establish that for a particular recipient the sound quality delivered by purely extra-cochlear stimulation is poor and can be improved by mixing in a certain fraction of intra-cochlear current. The sound quality improves as the fraction of intra-cochlear current is increased up to, say, 50% and after that increasing the fraction of intra-cochlear current does not improve the sound quality any further. In this case the clinician can optimally set the fraction of intra-cochlear current to 50% so that the recipient receives optimum sound quality and the longest battery life that achieved that sound quality. Or if the recipient favored a longer battery life over improved sound quality the ratio of intra-cochlear current may be set to less than 50% in order to trade off longer battery life with reduce sound quality.

In another example, a clinician establishes that the sound quality does not vary greatly with the fraction of intra-cochlear to intra-cochlear current so the fraction of intra-cochlear current would be likely to be zero in order to optimize battery life. However, if the fraction of intra-cochlear current is reduced below a20%, for example, the recipient experiences facial nerve stimulation. The clinician can then set the fraction of intra-cochlear current at, for example, 25%, to avoid facial nerve stimulation while maintaining a relatively low power consumption.

In order to vary the ratio of intra-cochlear to extra-cochlear current a user interface of, for example, the type shown in FIG. 4 may be employed, although it will be appreciated that any method of providing a user with the means to vary the ratio of intra-cochlear to extra-cochlear current can also be used. In FIG. 4 the user can drag and drop a slider marker on a computer screen. The user places the slider in the desired spot and the computer reads the position and allocates the ratio of intra-cochlear to extra-cochlear current according to the position of the slider. If the user places the slider to the far left position then the current in entirely intra-cochlear. If the user places the slider entirely to the right the current is entirely extra-cochlear. If the user places the slider in between the two extremes then the ratio of intra-cochlear to extra-cochlear current is determined according to the position of the slider. The ratio of currents can be determined linearly according to the position of the slider. If, for example, the slider is placed 80% towards the left then the proportion of intra-cochlear current could be set at 80%. If 20% towards the left then the proportion could be set to 20% and so on. It is also possible to use a non-linear function or a deterministic function to adjust the ratio of currents according to the position of the slider. If for example the slider is placed 80% towards the left then a formula or look up table is used to set the proportion of intra-cochlear current and this can, for example, result in a proportion of, say 60%.

It should be appreciated that FIG. 3 does not necessarily represent actual performance of battery life or auditory performance but simply illustrates the relationship between these variables and monopolar and bipolar stimulation.

Figure 5:
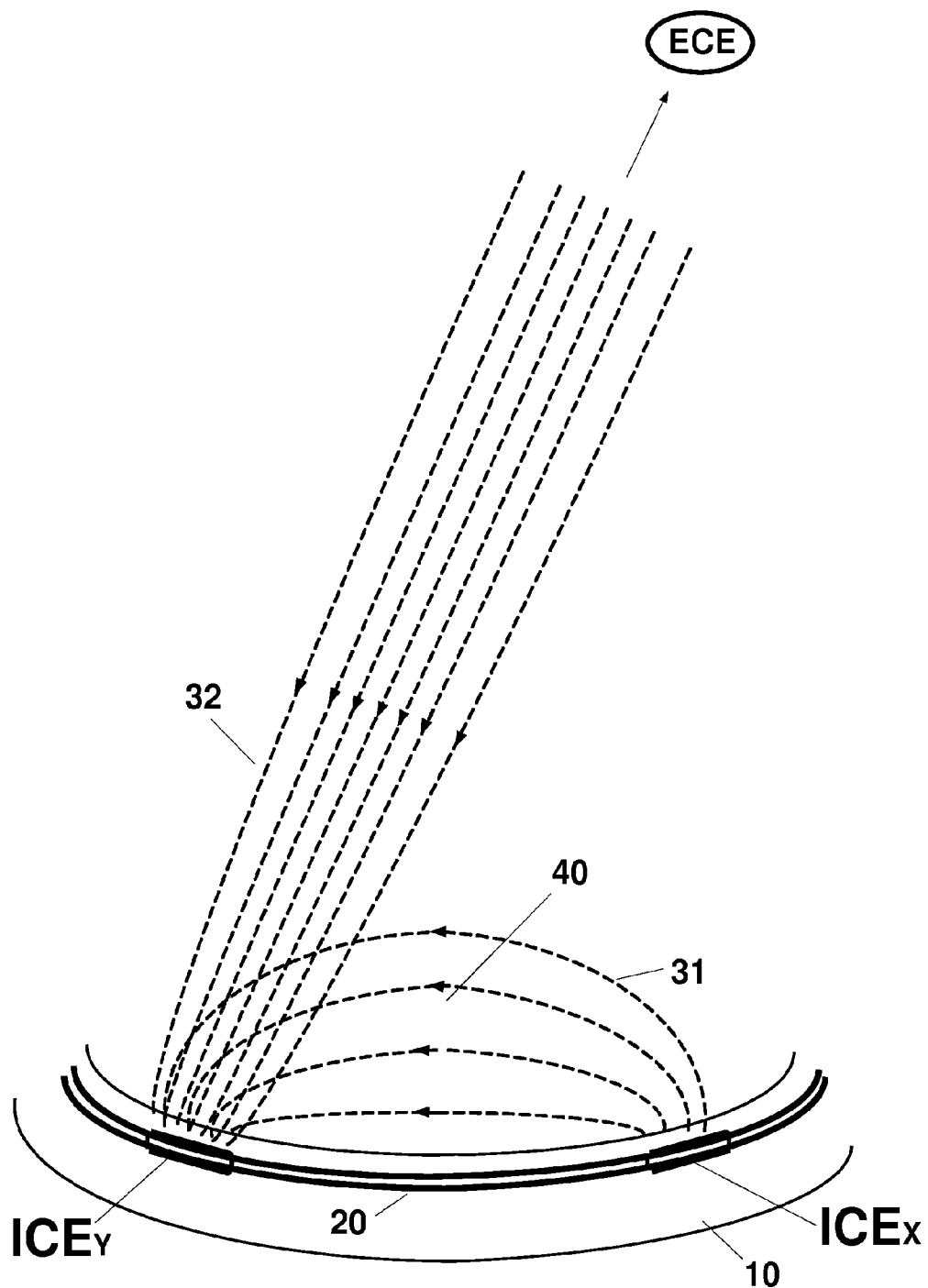
FIG. 5 is a schematic illustration of simultaneous intra-cochlear and extra-cochlear stimulation within the neural structures.

A simplified one-dimensional diagram of the current distribution for this approach is shown in FIG. 5. An electrode array 20 is shown within a section of the scala tympani 10. Electrode array 20 includes electrodes $ICE_x$ and $ICE_y$, each of which are connected to conductors (not shown) which deliver the stimuli to the electrodes. Also present, is an extra-cochlear electrode ECE. Neurons are located, in particular, in the region generally designated as 40 inside the curve of the scala tympani, including the modiolus and related structures. It should be appreciated that the representation in FIG. 5 is a simplified representation and does not attempt to model the real current paths which are in practice more complex and modified by the anatomy of the cochlea and surrounding structures.

Dashed lines 31 represent current that flows between electrodes $ICE_x$ and $ICE_y$. Dashed lines 32 represent current that flows to/from the extra cochlear electrode ECE, which in most cases would be located out of the plane of this view, but is shown in FIG. 5 for ease of understanding. A specific implementation of this approach, in terms of a method and illustrative circuitry, will now be discussed. This approach uses simultaneous intra-cochlear and extra-cochlear stimulation, with biphasic constant current stimulation simultaneously on two ICEs, and on one of these ICEs and an ECE, using a single current source.

The constant stimulation current provided by the current source is split between flows from ECE and $ICE_x$ to $ICE_y$ during phase 1 (as shown in FIG. 5), and from $ICE_y$ to $ICE_x$ and the ECE during phase 2 (current flowing in the opposite direction to that shown in FIG. 5).

Depending on the switch configuration of the electrodes, another simultaneous stimulation mode can be realized, in the form of a triphasic pulse, which achieves charge balance over three phases, as follows:

1. simultaneous stimulation between $ICE_x$ and $ICE_y$ and ECE and $ICE_y$ during phase 1,
2. simultaneous stimulation between $ICE_x$ and $ICE_y$ and stimulation between ECE and $ICE_x$ during phase 2; and
3. $ICE_x$ and $ICE_y$ to the ECE during phase 3.

The electrical charge delivered by the ECE and each of the intra-cochlea electrodes ($ICE_y$ during phase 1 and $ICE_x$ during phase 2) is balanced during phase 3.

Figure 6A:
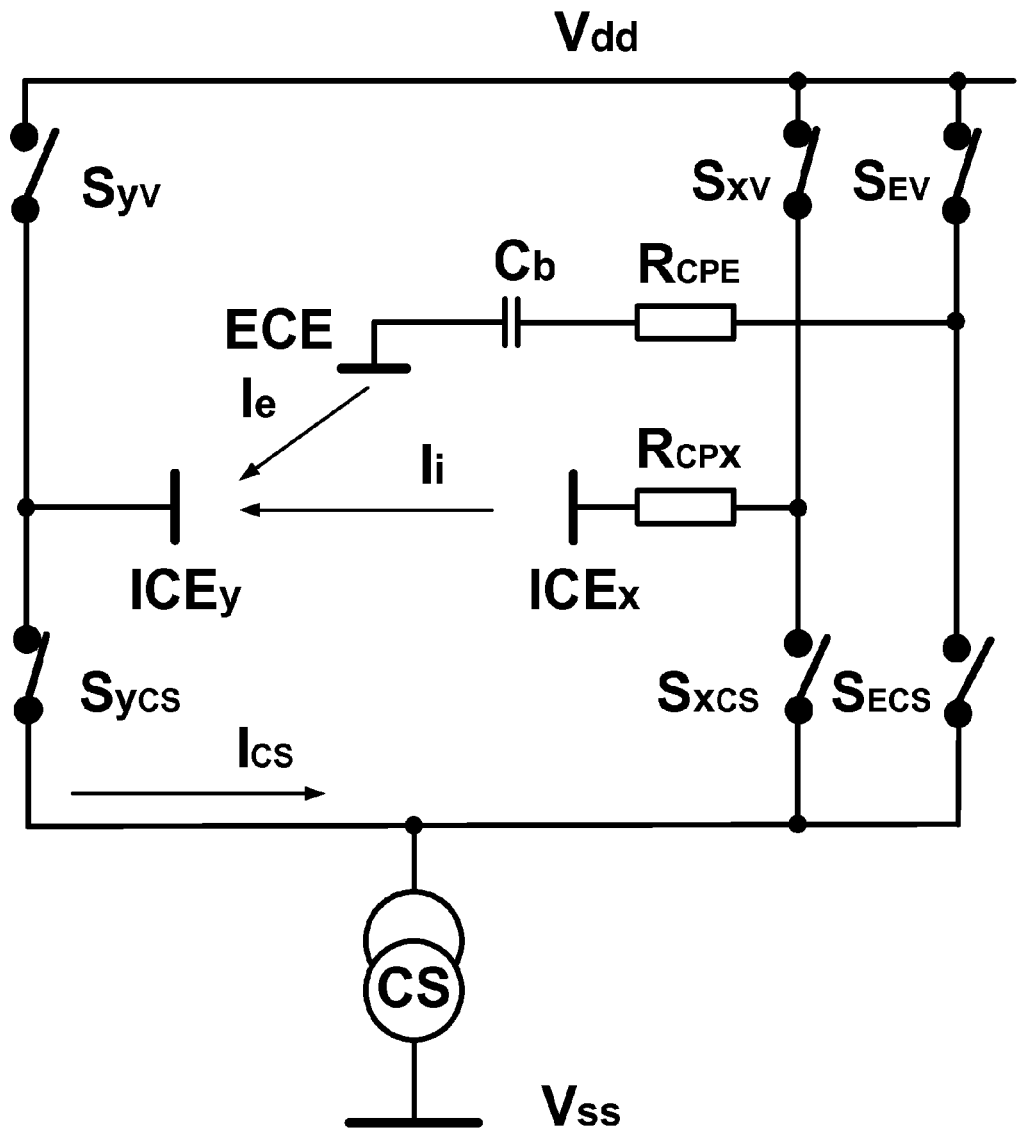
FIG. 6a illustrates a schematic circuit diagram of one embodiment during phase one of stimulation.
Figure 6B:
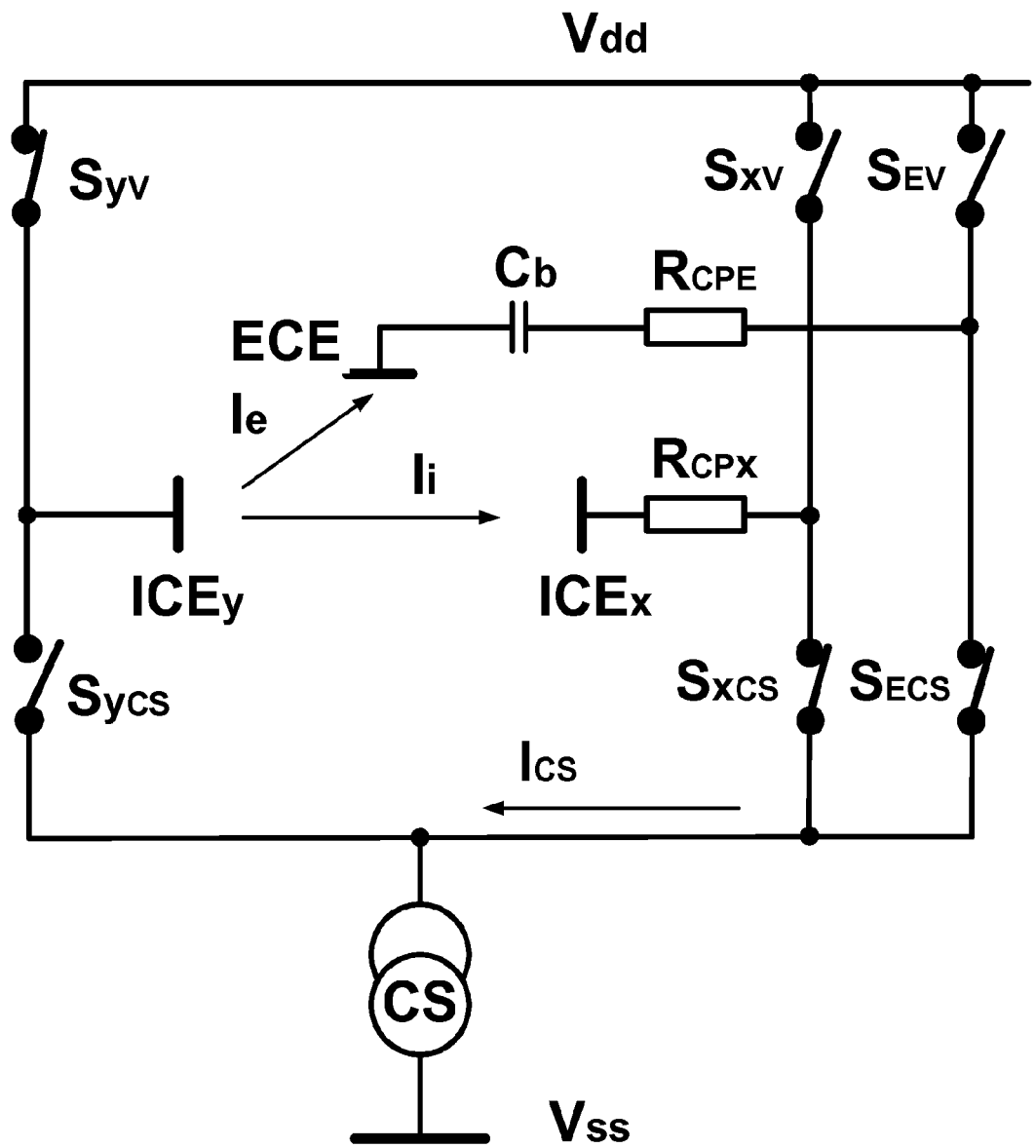
FIG. 6b illustrates a schematic circuit diagram of the embodiment of FIG. 6a during phase two of stimulation.

An example of a simplified block diagram of a circuit for simultaneous intra-cochlear and extra-cochlear stimulation with a single current source and one or more programmable resistors is shown in FIG. 6a and FIG. 6b. FIG. 6a represents phase 1 and FIG. 6b represents phase 2 of the biphasic stimulation. A biphasic current flows, in this example, simultaneously between two ICEs, and between one of these ICEs and an ECE. The elements of FIGS. 6a and 6b are as follows:

CS is the current source;
$V_{dd}$ is the power supply rail;
ECE is the extra-cochlear electrode;
$ICE_x$ is an intra-cochlear electrode;
$ICE_y$ is an intra-cochlear electrode, adjacent to $ICE_x$;
$R_{CPX}$ is a programmable resistor (resistive circuitry) connected in series with the intra-cochlear electrode $ICE_x$;
$R_{CPE}$ is a programmable resistor (resistive circuitry) connected in series with the extra-cochlear electrode ECE;
$C_b$ is a DC blocking capacitor connected in series with the extra-cochlear electrode ECE;
$S_{EV}$ and $S_{ECS}$ are the associated switches to the power supply rail and the current source for ECE;
$S_{xv}$ and $S_{xcs}$ are the associated switches to the power supply rail and the current source for $ICE_x$;
$S_{yv}$ and $S_{ycs}$ are the associated switches to the power supply rail and the current source for $ICE_y$;
$I_i$ is the intra-cochlear stimulation current;
$I_e$ is the extra-cochlear stimulation current; and
$I_{cs}$ is the total stimulation current ($I_{cs}=I_i+I_e$), and is the current source output current $I_{cs}$.

It should be appreciated that in this and other embodiments disclosed herein, the term "switch" is used to describe the function that occurs in the electrical circuit rather than implying that a physical switch is necessary. In an integrated circuit, for example, it is typical to use a transistor to act as a switch and any other element which performs the same or similar function is also envisaged.

During phase 1, illustrated in FIG. 6a, the stimulation current splits between the ECE and an intra-cochlear $ICE_x$ electrode (both indifferent electrodes—connected to $V_{dd}$ through $S_{EV}$ and $S_{xv}$ respectively) and flows from these two electrodes to another intra-cochlear electrode $ICE_y$ (active electrode—connected to the Current Source through the $S_{ycs}$ switch) creating an extra-cochlear stimulation circuit (ECE to $ICE_y$) and an intra-cochlear stimulation circuit (ECE to $ICE_x$). The total stimulation current $I_{cs}$ consists of the intra-cochlear current (between electrodes $ICE_x$ and $ICE_y$) and the extra-cochlear current $I_e$ (between electrodes ECE and $ICE_y$). The total stimulation current $I_{cs}$ is a constant value, that is, $I_{cs}=I_i+I_e$=constant. Resistive circuitry (programmable resistor) $R_{cpx}$ connected in series with the indifferent (connected to $V_{dd}$) intra-cochlear electrode $ICE_x$ dictates what proportion the intra-cochlear and extra-cochlear $I_e$ stimulation currents are of the proportion of the total stimulation current $I_{cs}$.

During phase 2, illustrated in FIG. 6b, the intra-cochlear $ICE_x$ and the extra-cochlear ECE electrode become active (connected to the current source through switches $S_{xcs}$ and $SEC_S$) and the intra-cochlear electrode $ICE_y$ becomes indifferent (connected to $V_{dd}$ through $S_{yv}$ switch). The intra-cochlear and the extra-cochlear Ie currents change direction, but not amplitude ($L_{cs}=I_i+I_e$=constant) and flow from electrode $ICE_y$ to $ICE_x$ and ECE electrodes.

The resistive circuitry's value can be set from 0 (short circuit) to infinity (open circuit) in order to obtain an appropriate ratio of the intra-cochlear and extra-cochlear stimulation currents, so that the appropriate tradeoff is made between battery life and auditory performance. Any suitable form of controllable resistor can be used, preferably so that such a resistor is associated with each electrode. In a preferred form, the resistor is fabricated as part of the IC for the implant.

The stimulation current value is set by the current source and depends only on the parameters of the current source. The value of the intra-cochlear and extra-cochlear $I_e$ current depend on the impedance of the intra-cochlear current path and extra-cochlear current path, respectively. The proportion of current in each path is achieved by the use of a programmable resistor(s) connected in the current path (intra-cochlear and/or extra-cochlear). Increasing the value of the programmable resistor will increase the impedance of the associated current path, and accordingly will decrease the current flow through this current path. As the total current is constant, this will in turn increase the current flow through the other current path. The extreme value or open circuit of the programmable resistor will stop the current flow through the associated current path (intra-cochlear or extra-cochlear). Thus the full stimulation current will flow only extra-cochlear or intra-cochlear. Examples of resistance values and corresponding current values $I_e$ and appear below.

Intracochlea Stimulation
$R_{CPE}=\infty$ (open circuit), $I_e=0$
Rcpx=0 (short circuit), $I_i=I_{cs}$
Extracochlea Stimulation
$R_{CPE}=0$ (short circuit), $I_e=I_{cs}$
$R_{cpx}=\infty$ (open circuit), $I_i=0$
Simultaneous Intracochlear-Extracochlea Stimulation
$I_e+=I_{cs}$ (constant value)
If $R_{cpx}=R_{CPE}=0$ (short circuit), then the ratio extracochlea/intracochlea current is:

$$I_e/1=Z_i/Z_e$$

where:
$Z_i$—is the tissue impedance between the ECE and $ICE_y$
$Z_i$—is the tissue impedance between $ICE_x$ and $ICE_y$
If $R_{CPE}$ remains zero (short circuit) and $R_{CPX}$ increases its value up from zero, then $I_e$ increases and $I_i$ decreases.
If $R_{CPX}$ remains zero (short circuit) and $R_{CPE}$ increases its value up from zero, then $I_i$ increases and $I_e$ decreases.
In another example arrangement:
$R_{CPE}=0$ (short circuit), $R_{CPX}$=for example 10 k ohms $I_e>>I_i$ ($I_e+I_i=I_{es}$– constant value)
If $R_{CPE}$ increases its value up from zero to 10 k ohms and $R_{CPX}$ decreases from 10 k ohms to zero, then $I_e$ decreases and $I_i$ increases (while $I_e+I_i=I_{es}$–constant value).
When $R_{CPX}=0$ (short circuit), $R_{CPE}=10$ k ohms, then $I_i>>I_e$ ($I_e+I_i=I_{es}$–constant value)

A particular advantage of implementations of this embodiment is that there is great flexibility in the way currents can be delivered. For example, more than two paths (for example three) between different combinations of ICEs and the ECE can be used simultaneously. There are stimulation modes in addition to bipolar stimulation that use current between the ICEs only. For example, tripolar stimulation mode usually involves passing current to or from a central ICE and simultaneously passing current of opposite polarity from or to the two ICEs on either side of the central electrode. Using this example, currents in the two ICEs can be reduced by a certain amount and an equal amount of current can be supplied by an ECE to achieve a similar effect to that described above for bipolar stimulation. Indeed for any stimulation mode using only ICEs current flow can be introduced to or from an ECE to achieve a similar effect. The ICEs stimulated are not required to be adjacent, as shown in the example above, but any two, three or more arbitrary ICEs can be used for ECE—ICE stimulation.

The current flow through the extra-cochlea and intra-cochlea current paths can be monitored and controlled, by measuring the voltage over the programmable resistor(s) or between the electrodes in use and providing feedback by altering the value of the programmable resistor(s). This provides an additional control measure to better control the current flow.

Figure 6C:
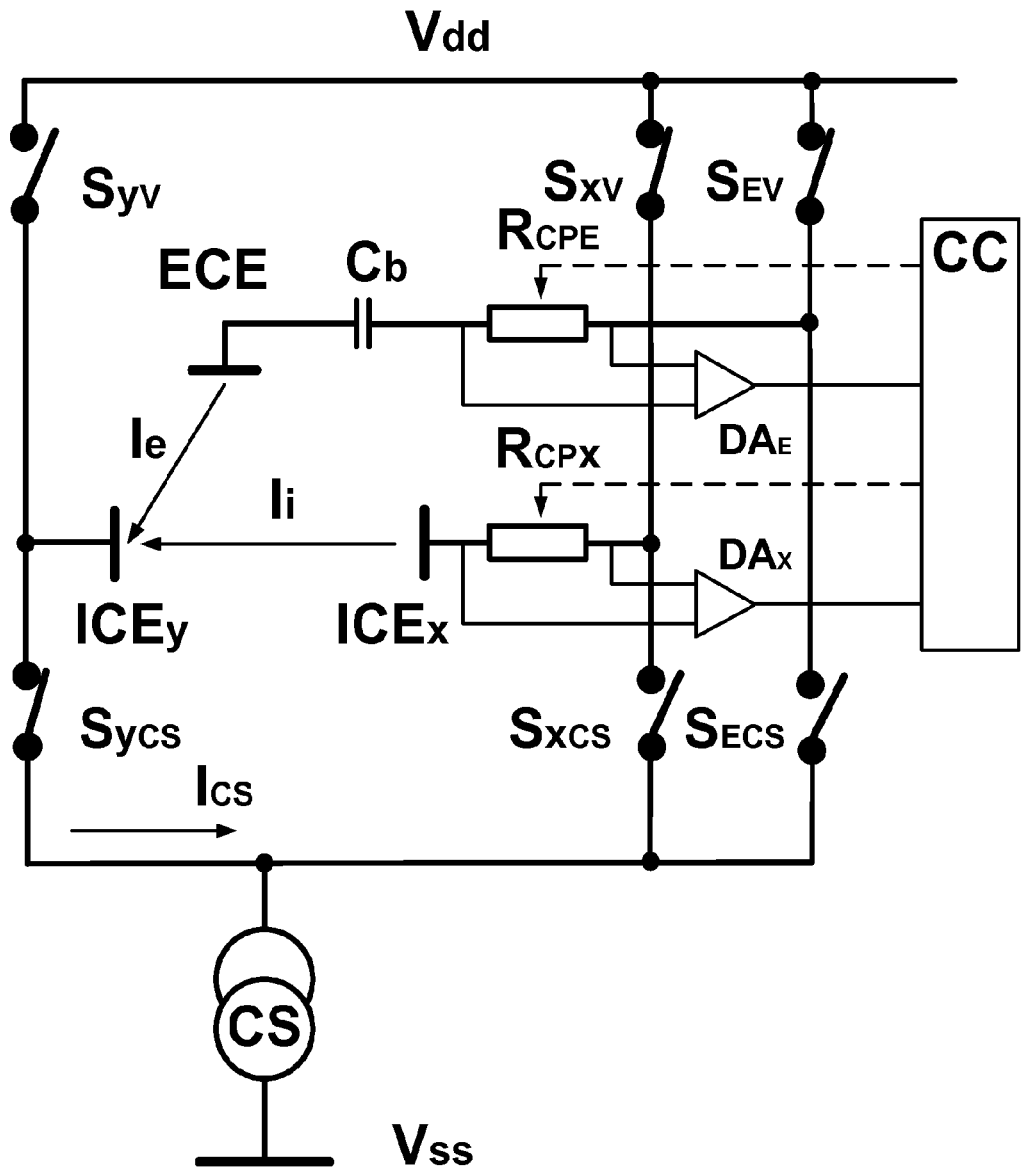
FIG. 6c illustrates a schematic circuit diagram of the implementation of FIG. 6a for measurement and control of the stimulation current(s)

An example is shown in FIG. 6c, where DA is a differential amplifier, and CC—is a control circuit and all other elements are as referenced with respect to FIGS. 6a and 6b.

The voltage over the programmable resistor $R_{CPX}$ ($R_{CPE}$) is proportional to the value (amplitude) of the current that flows through $R_{CPX}$ ($R_{CPE}$) respectively through the intra-cochlear (extra-cochlear) current path. Any change of the value of the programmable resistor $R_{CPX}$ ($R_{CPE}$) causes re-distribution between the intra-cochlea and extra-cochlear current flows (current steering) while the sum of both current flows (the total stimulation current generated by the current source) remains unchanged (constant).

The voltage over the programmable resistors $R_{CPX}$ ($R_{CPE}$) is measured by the corresponding differential amplifier $DA_x$ ($DA_E$) and is indicative of the value of the current that flows through the intra-cochlear (extra-cochlear) current path. The control circuit CC, responsive to the output from the differential amplifiers, can vary the value of the programmable resistor $R_{CPX}$ ($R_{CPE}$) in order to obtain and/or maintain the desired intra-cochlear and extra-cochlear current flow (the desired current steering).

FIGS. 7a, 7b, 7c and 7d illustrate an alternative embodiment. In this arrangement, the extra-cochlear electrode ECE is connected to the power supply rail $V_{dd}$ through switch $S_{EV}$ during phase 1 and phase 2 and to the Current Source through switch $S_{ECS}$ during phase 3.

Figure 7A:
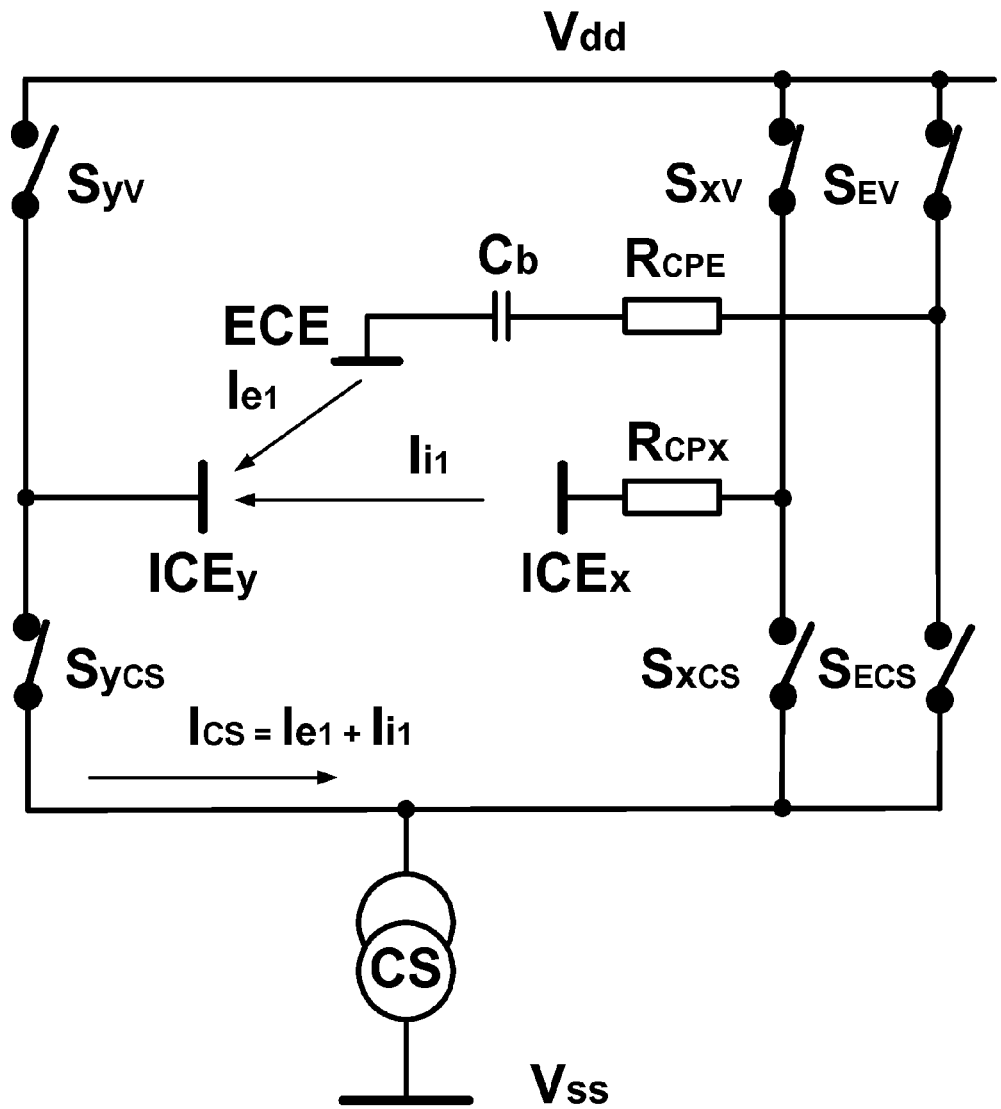
FIG. 7a illustrates a schematic circuit diagram of a second embodiment during phase 1 of stimulation.

During phase 1, as shown in FIG. 7a, an intra-cochlear current Ili flows from intra-cochlear electrode $ICE_x$ to intra-cochlear electrode $ICE_y$, creating an intra-cochlear stimulation circuit ($ICE_x$ to $ICE_y$), and an extra-cochlear current $I_{e1}$ flows from extra-cochlear electrode ECE to intra-cochlear electrode $ICE_y$, creating an extra-cochlear stimulation circuit (ECE to $ICE_y$).

Figure 7B:
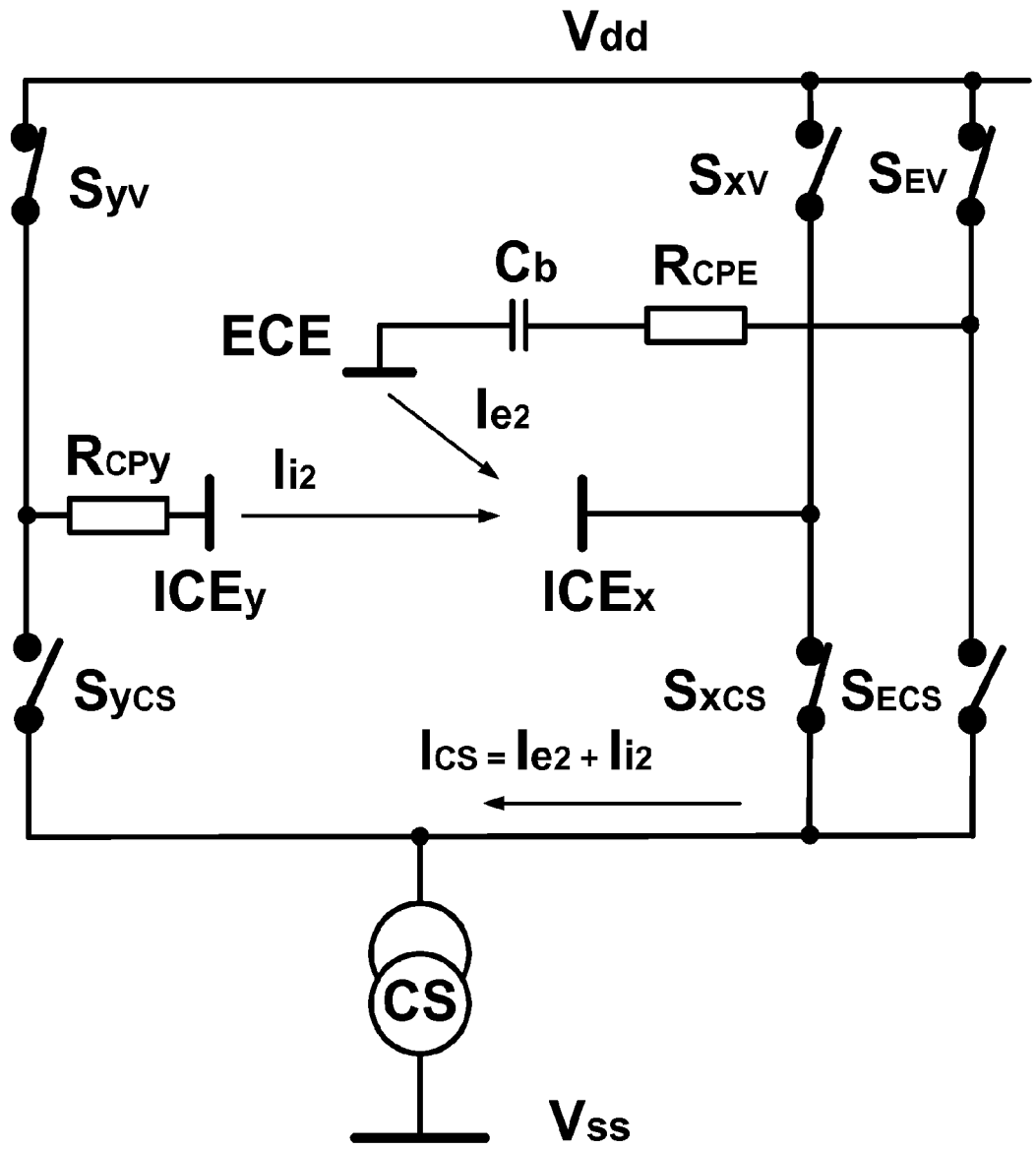
FIG. 7b illustrates a schematic circuit diagram of a second embodiment during phase 2 of stimulation.

During phase 2, shown in FIG. 7b, the intra-cochlear current $I_{i2}$ flows from intra-cochlear electrode $ICE_y$ to intra-cochlear electrode $ICE_x$, creating an intra-cochlear stimulation circuit ($ICE_x$ to $ICE_y$), and the extra-cochlear current $I_{e2}$ flows from extra-cochlear electrode ECE to intra-cochlear electrode $ICE_x$ creating an extra-cochlear stimulation circuit (ECE to $ICE_x$). The electrical charge delivered by the intra-cochlear electrodes ($ICE_x$, $ICE_y$) during phase 1 ($I_{i1}$ FIG. 7a) is balanced during phase 2 ($I_{i2}$, FIG. 7b). The intra-cochlear current $I_{i2}$ (Phase 2) is equal to the intra-cochlear current $I_{i2}$ (Phase 1A): $I_{i2}=I_{i1}$ The extra-cochlear current $I_{e2}$ (Phase 2) is equal to the extra-cochlear current $I_{e2}$ (Phase 1): $I_{e2}=I_{e1}$.

Figure 7C:
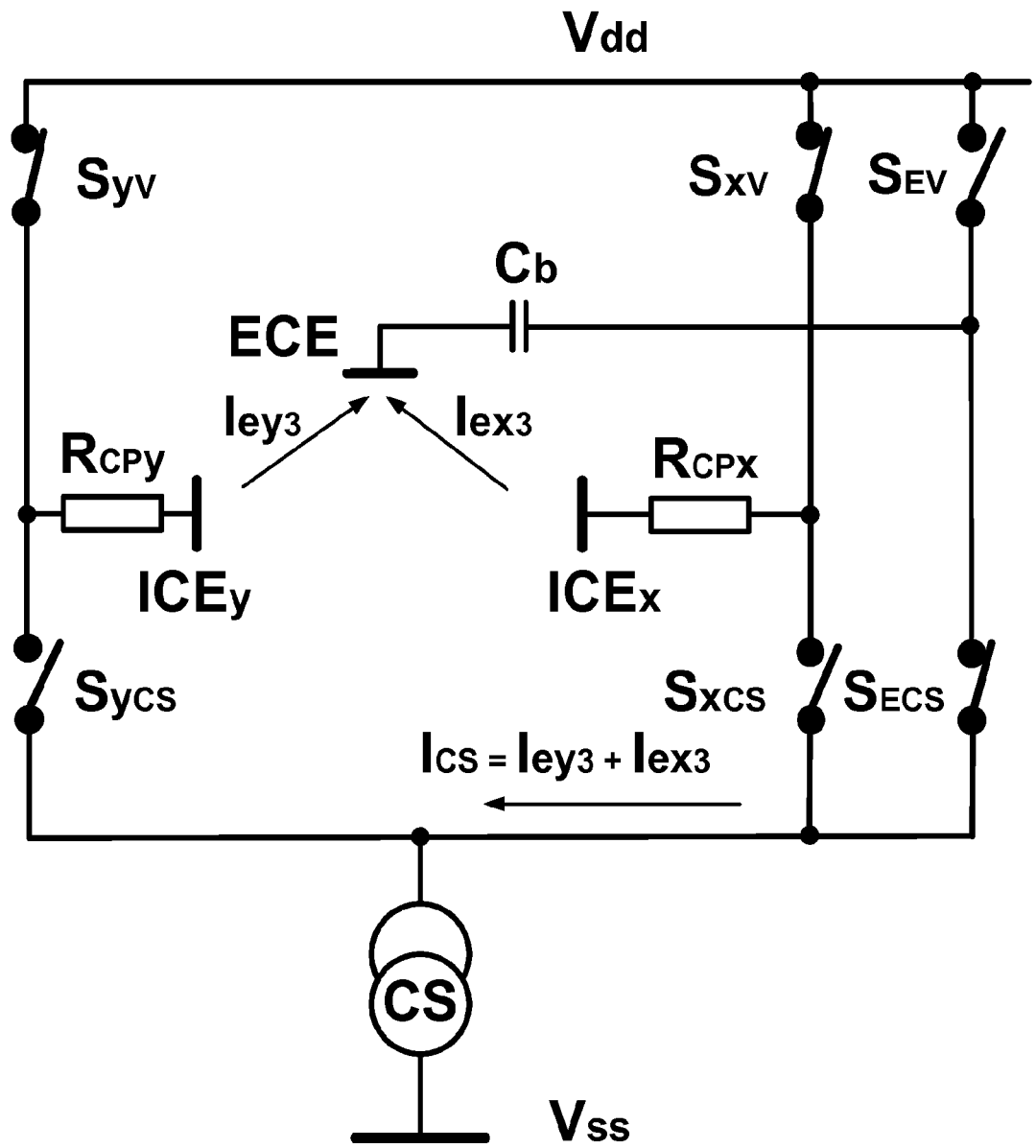
FIG. 7c illustrates a schematic circuit diagram of a second embodiment during phase 3 of stimulation.
Figure 7D:
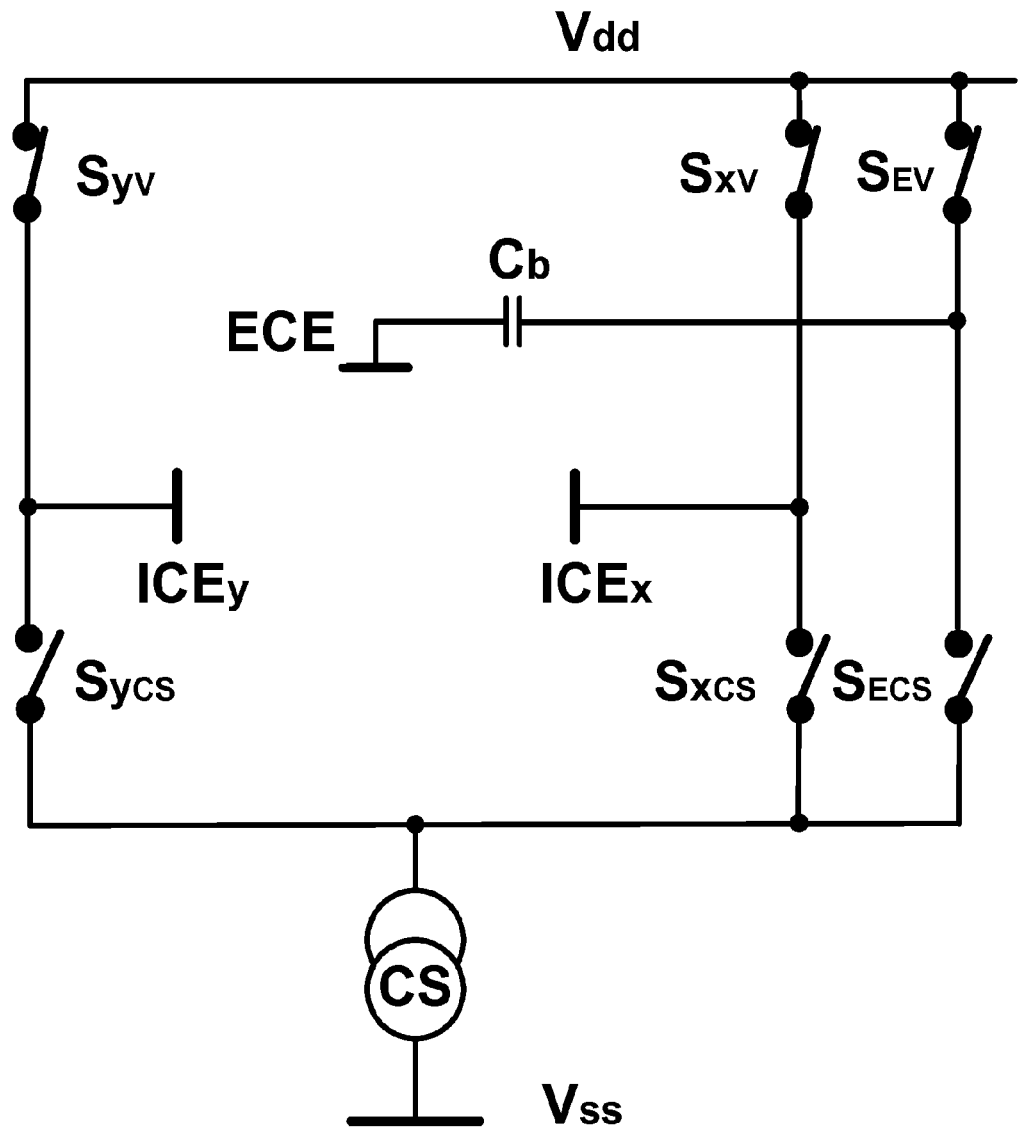
FIG. 7d illustrates a schematic circuit diagram of a second embodiment during an inter-frame gap.

During phase 3, shown in FIG. 7c, the extra-cochlear current flows from intra-cochlear electrode $ICE_x$ ($I_{ex3}$) and intra-cochlear electrode $ICE_y$ ($I_{ey3}$) to extra-cochlear electrode ECE creating an extra-cochlear stimulation circuit (ECE to $ICE_y$ and to $ICE_x$). The electrical charge delivered by the extra-cochlear electrode ECE and each of the intra-cochlear electrodes ($ICE_y$ during phase 1 and $ICE_x$ during phase 2; FIG. 6a, 6b) is balanced during phase 3 (FIG. 6c). The extra-cochlear current $I_{ey3}$ (Phase 3) is equal to the extra-cochlear current $I_{e1}$ (Phase 1) and the extra-cochlear current $I_{ex3}$ (Phase 3) is equal to the extra-cochlear current $I_{e2}$ (Phase 2): $I_{ey3}=I_{e1}$ and $I_{ex3}=I_{e2}$ During the inter-frame gap, between successive stimuli, all electrodes are short circuited (connected to the $V_{dd}$ rail)—FIG. 7d.

Figure 8A:
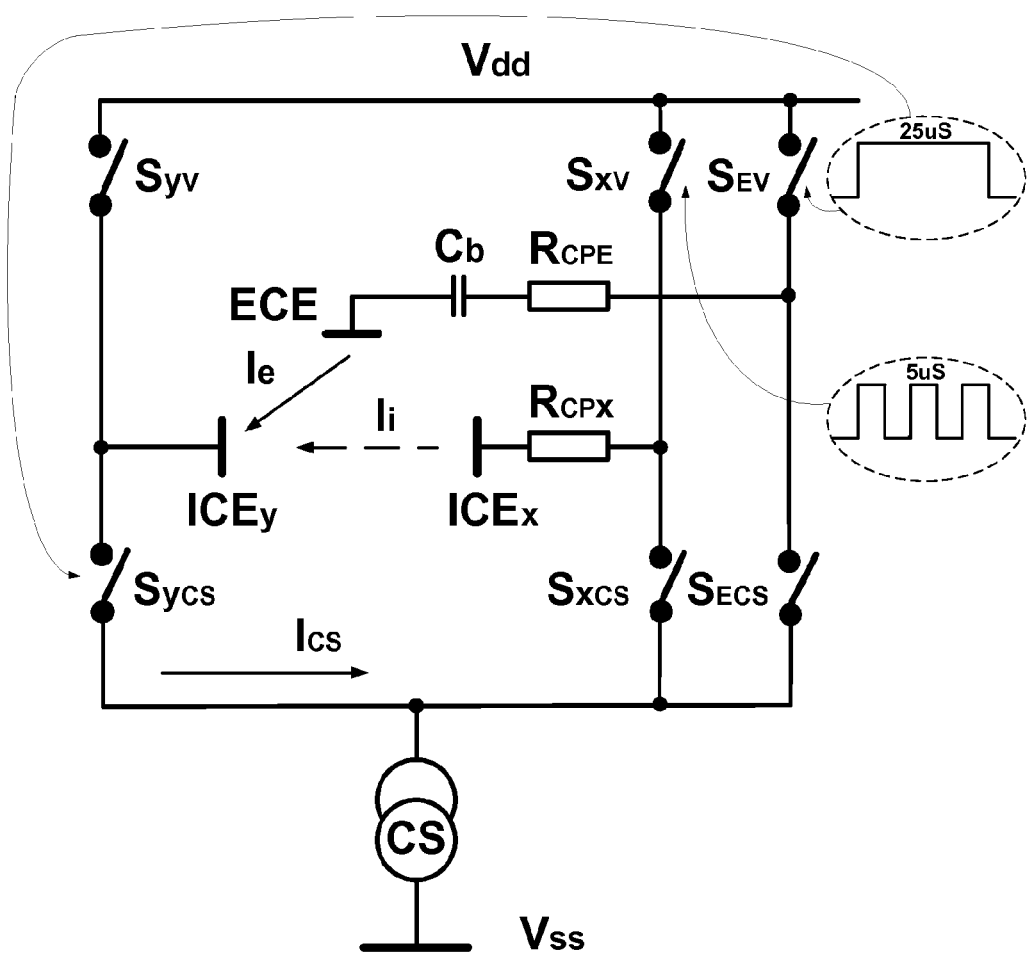
FIG. 8a is a schematic circuit diagram illustrating the application of pulse width modulation to another embodiment during phase one.
Figure 8B:
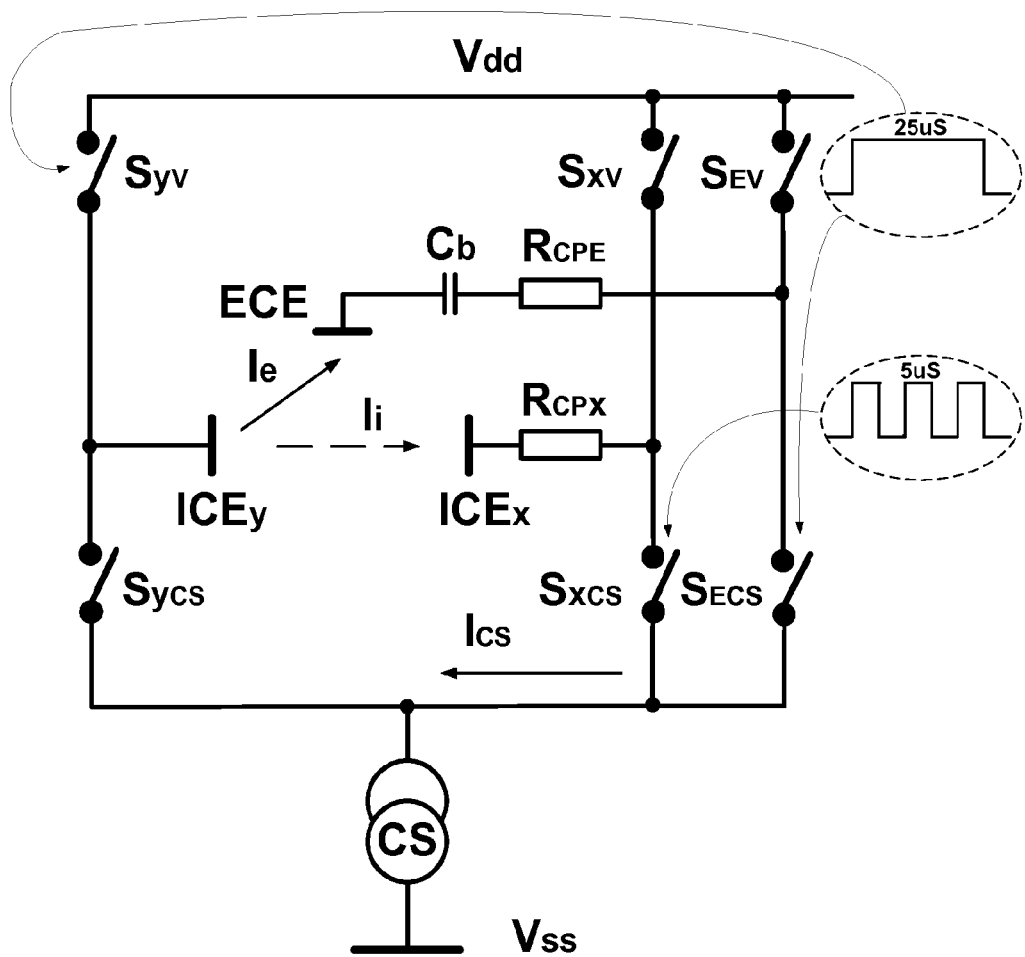
FIG. 8b is a schematic circuit diagram of the circuit of FIG. 8a, during phase two.

FIGS. 8a and 8b illustrate a circuit similar to FIG. 6a and FIG. 6b, but in which the switch timing is controlled by a timing circuit.

The switches are controlled so that the timing of delivery of currents is coordinated (synchronized). During a 25 microsecond extra-cochlear stimulation pulse, three 5 μs intra-cochlear stimulation pulses with a 5 μs gap between them can be applied. During the gaps of the intra-cochlear stimulation pulses only extra-cochlear stimulation current will flow (monopolar stimulation). During the intra-cochlear stimulation pulses extra-cochlear and intra-cochlear stimulation currents will flow simultaneously (simultaneous intra-cochlear-extra-cochlear stimulation).

Simultaneous intra-cochlear and extra-cochlear stimulation can be provided in devices in which multiple current sources are employed. In a manner similar to the one current source configuration, the amount of current flowing from the intra-cochlea electrode(s) and at least one extra-cochlea electrode can be selected for multiple current sources configurations employing programmable resistors.

Figure 9A:
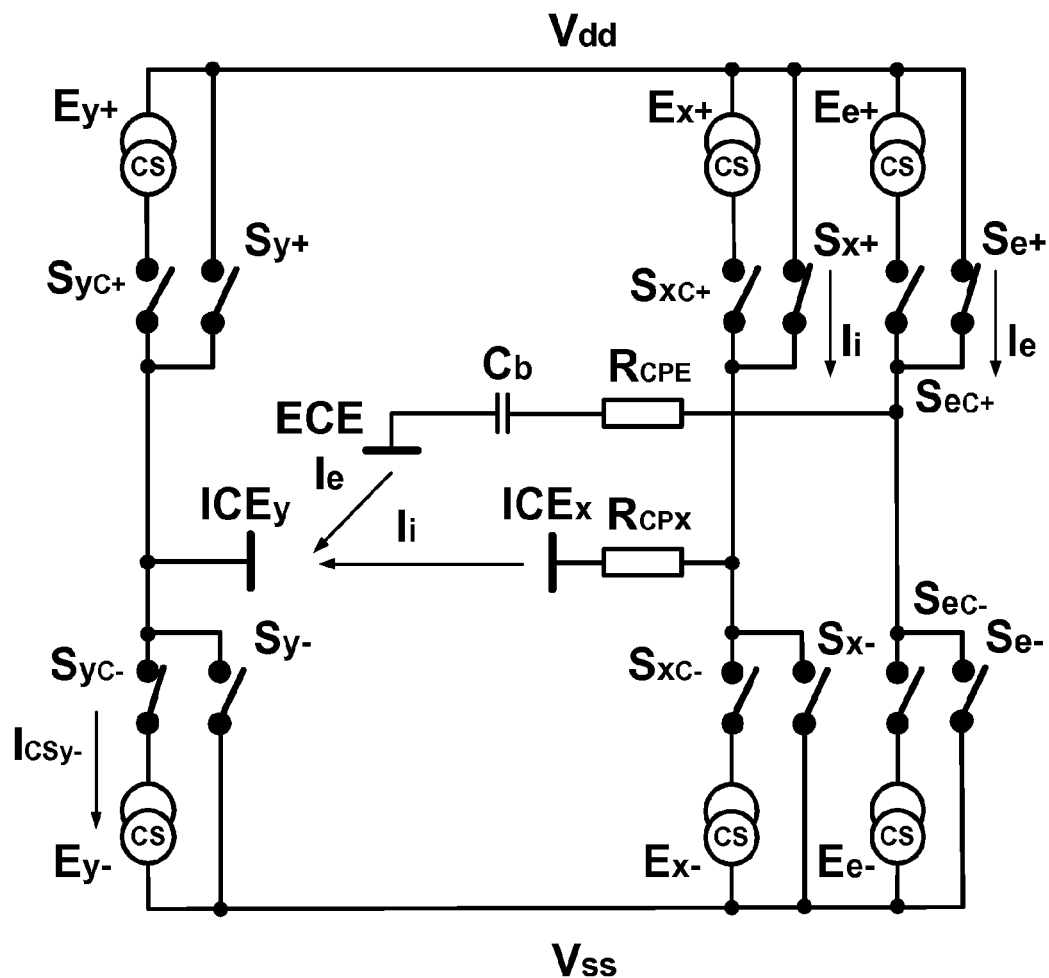
FIG. 9a illustrates a schematic circuit diagram of a multiple current source embodiment during phase one of stimulation.
Figure 9B:
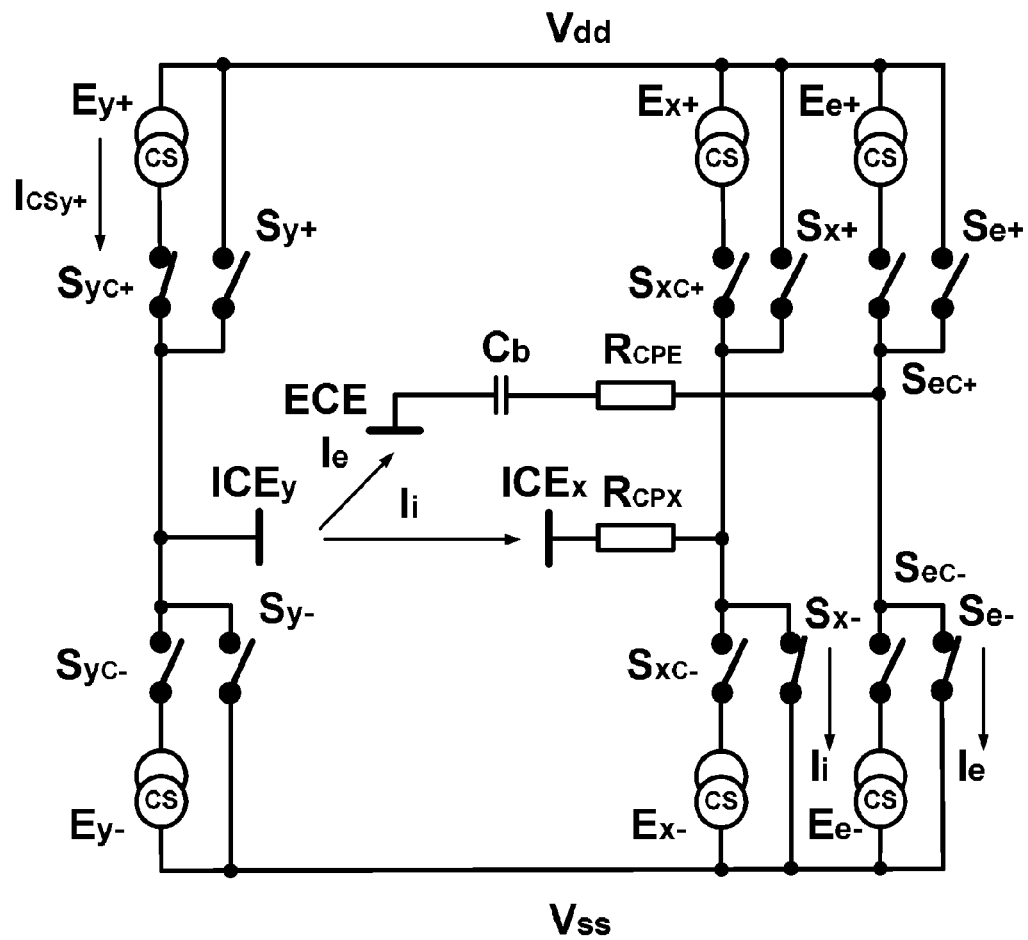
FIG. 9b illustrates a schematic circuit diagram of a multiple current source embodiment during phase two of stimulation.

A configuration with two current sources (or one bipolar current source) for each electrode that stimulates intra-cochlea and extra-cochlea simultaneously is depicted in FIGS. 9a and 9b, where:

$V_{dd}$ is the positive power supply rail (positive polarity)

$V_{ss}$ is the negative power supply rail (negative polarity)

$ICE_y$ is an intra-cochlear electrode $E_y+CS$, $E_y-CS$—two current sources or a bipolar current source associated to the $ICE_y$ $S_y+$ is a switch connecting the $ICE_y$ to the $V_{dd}$ power supply rail $S_y-$ is a switch connecting the $ICE_y$ to the $V_{ss}$ power supply rail $S_{yc}+$ is a switch connecting the $ICE_y$ to the $E_y+CS$ current source $S_{yc}-$ is a switch connecting the $ICE_y$ to the $E_y-CS$ current source $ICE_x$ is an intra-cochlear electrode $E_x+CS$, $E_x-CS$—two current sources or a bipolar current source associated to the $ICE_x$ Sx+ is a switch connecting the $ICE_x$ to the $V_{dd}$ power supply rail $S_x-$ is a switch connecting the $ICE_x$ to the $V_{ss}$ power supply rail $S_{xc}+$ is a switch connecting the $ICE_x$ to the $E_x+CS$ current source $S_{xc}-$ is a switch connecting the ICEx to the Ex+CS current source $R_{cpx}$ is a programmable resistor connected in series with $ICE_x$ ECE is an extra-cochlear electrode $E_e+CS$, $E_e-CS$—two current sources or a bipolar current source associated to the ECE $S_e+$ is a switch connecting the ECE to the $V_{dd}$ power supply rail $S_e$ is a switch connecting the ECE to the $V_{ss}$ power supply rail $S_{ec}+$ is a switch connecting the ECE to the $E_e+CS$ current source $S_{ec}-$ is a switch connecting the ECE to the $E_e-CS$ current source $R_{CPE}$ is a programmable resistor connected in series with ECE $I_i$ is the intra-cochlear stimulation current $I_e$ is the extra-cochlear stimulation current $I_{CSy-}$ is the current generated by the $E_y-CS$ ($I_{CSy-}=I_i+I_e$)

ICSy+ is the current generated by the $E_y+CS$ ($I_{CSy+}+I_i=+I_e$)

During phase 1, illustrated in FIG. 9a, the active electrode $ICE_y$ is connected to the $E_y-CS$ current source and the indifferent electrodes $ICE_x$ and ECE are connected to the power supply rail $V_{dd}$ via the programmable resistors $R_{cpx}$ and RIPE respectively. The stimulation current $I_{CSy}-$ is the sum of the intra-cochlear $I_e$ and the extra-cochlear $I_e$ currents.

The intra-cochlea current $I_i$ flows from the power supply rail $V_{dd}$ through the $S_x+$ switch, the programmable resistor $R_{cpx}$, the $ICE_x$ electrode, the tissue between $ICE_x$ and $ICE_y$, the active electrode $ICE_y$, the $S_{yc}-$ switch to the activated current source $E_y-CS$.

The extra-cochlea current $I_e$ flows from the power supply rail $V_{dd}$ through the Se+ switch, the programmable resistor $R_{CPE}$, the ECE electrode, the tissue between ECE and $ICE_y$, the active electrode $ICE_y$, the $S_{yC}-$ switch to the activated current source $E_y-CS$.

During phase 2, shown in FIG. 9b, the active electrode $ICE_y$ is connected to the $E_y+CS$ current source and the indifferent electrodes $ICE_x$ and ECE are connected to the power supply rail $V_{ss}$ via the programmable resistor $R_{CPX}$ and $R_{CPE}$ respectively. The stimulation current $I_{CSy}+$ is the sum of the intra-cochlear $I_i$ and the extra-cochlear $I_e$ currents ($I_{CSy}+= I_{CSy}-$).

The intra-cochlear current Ii flows from the activated current source $E_y+CS$ through the $S_{yC}+$ switch, the active electrode $ICE_y$, the tissue between $ICE_y$ and $ICE_x$, the $ICE_x$ electrode, the programmable resistor $R_{CPX}$, the $S_x-$ switch to the power supply rail $V_{ss}$.

The extra-cochlear current Ie flows from the activated current source $E_y+CS$ through the $S_{yC}+$ switch, the active electrode $ICE_y$, the tissue between $ICE_y$ and ECE, the ECE electrode, the programmable resistor $R_{CPE}$, the $S_e-$ switch to the power supply rail $V_{ss}$.

For each phase the indifferent electrodes are connected to the power supply rail with opposite polarity to the polarity of the activated current source associated with the active electrode.

The ratio of the intra-cochlear and extra-cochlear currents ($I_i/I_e$) is reciprocal to the ratio of the resistance of the intra-cochlear and extra-cochlear current paths:

$$I_i/I_e = (R_{CPE}+Z_e)/(R_{CPX}+Z_i)$$

where:
$Z_e$—is the tissue impedance between the ECE and $ICE_y$
$Z_i$—is the tissue impedance between $ICE_x$ and $ICE_y$ The resistance of the extra-cochlear current path consist of the programmable resistor $R_{CPE}$ connected in series with the tissue impedance ($Z_e$) between the ECE and $ICE_y$.

The resistance of the intra-cochlear current path consist of the programmable resistor Rcpx connected in series with the tissue impedance ($Z_i$) between the $ICE_x$ and $ICE_y$.

Thus, the configuration of FIGS. 9a and 9b allows the device to deliver intra-cochlear stimulation (bipolar stimulation), extra-cochlear stimulation (monopolar stimulation) or simultaneous intra-cochlear stimulation—extra-cochlear stimulation. Any electrode combinations within these configurations are envisaged.

A simultaneous extra-cochlear and intra-cochlear stimulation device can be configured with multiple stimulation electrodes and multiple current sources, where each electrode can be connected (independently of the others) to a bipolar current source (or to two current sources with opposite polarities) associated to it or to each of the power supply rails directly or via a programmable resistor.

Figure 10A:
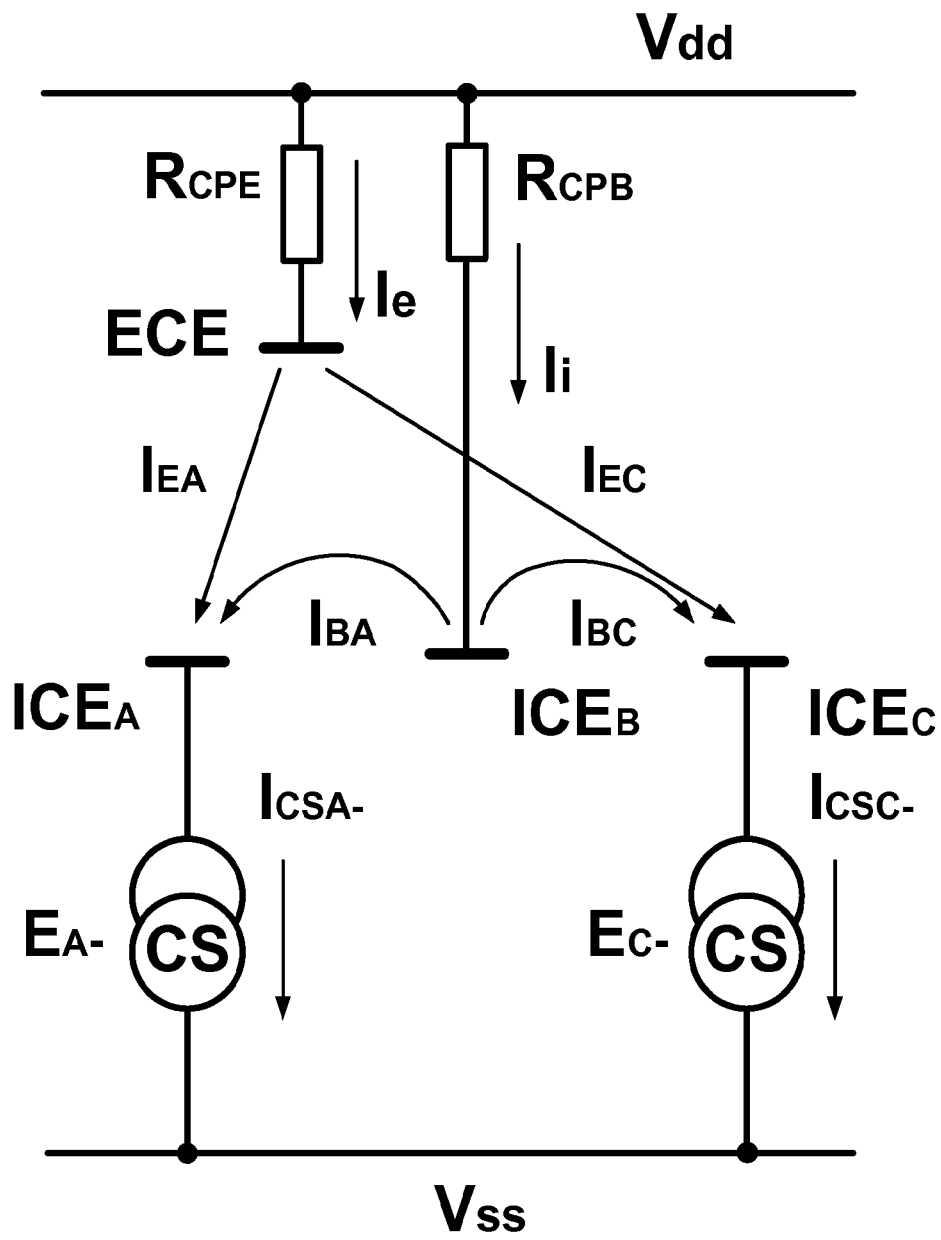
FIG. 10a illustrates a schematic circuit diagram of a second multiple current source embodiment during phase one of stimulation.
Figure 10B:
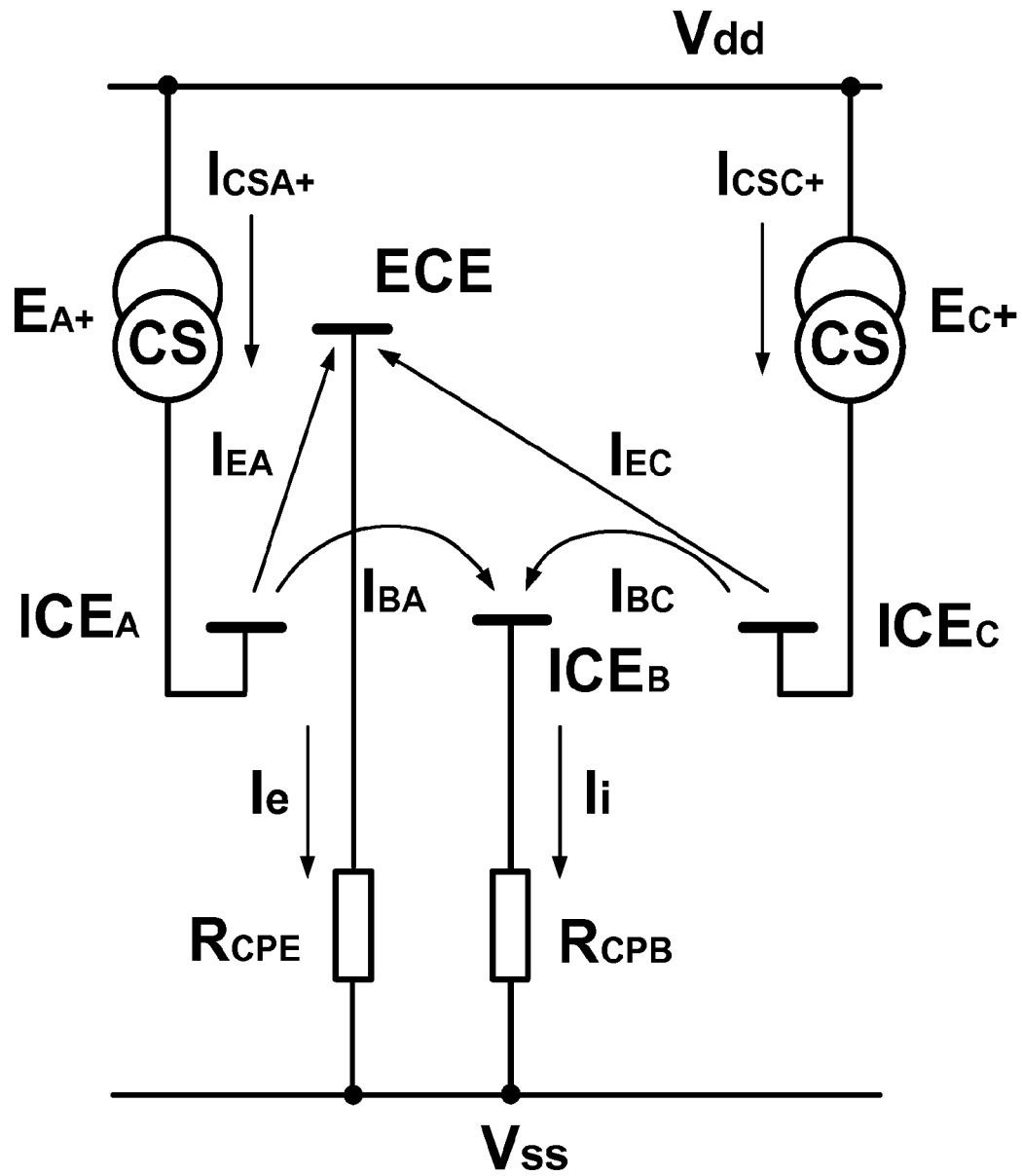
FIG. 10b illustrates a schematic circuit diagram of a second multiple current source embodiment during phase two of stimulation.

FIGS. 10a and 10b depict a configuration where two (more than one) active electrodes are used:

$ICE_A$ and $ICE_C$ are active intra-cochlear electrodes (each of them connected to its current source)

$ICE_B$ is an indifferent intra-cochlear electrode (connected to a power supply rail)

ECE is an indifferent extra-cochlear electrode (connected to a power supply rail)

$I_{EA}$ and $I_{EC}$ are extra-cochlear currents flow between ECE and $ICE_A$, $ICE_c$ respectively $I_{BA}$ and $I_{BC}$ are intra-cochlear currents flow between $ICE_B$ and $ICE_A$, $ICE_c$ respectively $E_A-CS$ is the activated current source associated to the $ICE_A$ (FIG. 10a)

$I_{CSA}-$ is the current generated by the $E_A-CS$ (FIG. 10a)

$E_c-CS$ is the activated current source associated to the $ICE_c$ (FIG. 10a)

$I_{csc}-$ is the current generated by the $E_c-CS$ (FIG. 10a)

For simplicity, all switches as well as the current sources of the indifferent electrodes are not shown.

Phase 1 is illustrated in FIG. 10a. The extra-cochlear current Ie flows from an indifferent extra-cochlear electrode ECE to the active intra-cochlear electrodes $ICE_A$ and $ICE_c$; ($I_e = I_{EA} I_{EC}$).

The intra-cochlear current $I_i$ flows from an indifferent intra-cochlear electrode $ICE_B$ to the active intra-cochlear electrodes $ICE_A$ and $ICE_{ci}$ ($I_i = I_{BA}+I_{BC}$)

The ratio of the intra-cochlear and extra-cochlear currents ($I_i/I_e$) is reciprocal to the ratio of the resistance of the intra-cochlear and extra-cochlear current paths.

The resistance of the extra-cochlear current path consist of the programmable resistor RIPE connected in series with the tissue impedance ($Z_e$) between the ECE and $ICE_A$, $ICE_c$.

The resistance of the intra-cochlear current path consist of the programmable resistor $R_{CPB}$ connected in series with the tissue impedance ($Z_i$) between the $ICE_B$ and $ICE_A$, $ICE_c$.

$$I_i/I_e = (I_{BA}+I_{BC})/(I_{EA}+I_{EC}) = (R_{CPE}+Z_e)/(R_{CPB}+Z_i)$$

The total stimulation current $I_{TS}$ is the sum of the currents generated by the activated current sources $E_A-CS$ and $E_c-CS$:

$$I_{TS} = I_{CSA} - I_{CSC} - = (I_{EA}+I_{BA}) + (I_{EC}+I_{BC})$$

The ratio of the currents flow to the active electrodes $ICE_A$ and $ICE_c$ is actually the ratio of the currents generated by the current sources associated to $ICE_A$ and $ICE_c$:

$$(I_{EA}+I_{BA})/(I_{EC}+I_{BC}) = I_{CSA}-/I_{CSC}-$$

In phase 2, the second phase of biphasic stimulation, shown in FIG. 10b, the current sources of the active electrodes, as well as the indifferent electrodes, change polarity, resulting in reversal of the direction of all the current flows. The stimulation currents (intra-cochlear and extra-cochlear) change direction but not amplitude (in order to have charge balanced stimulation), hence the above equations for phase 1 are valid for phase 2.

The embodiment of FIG. 9a, FIG. 9b, FIGS. 10a and 10b describes a stimulation circuit in which there are multiple current sources and the current supplied to a stimulation circuit is controlled by a variable resistance circuit.

Figure 11:
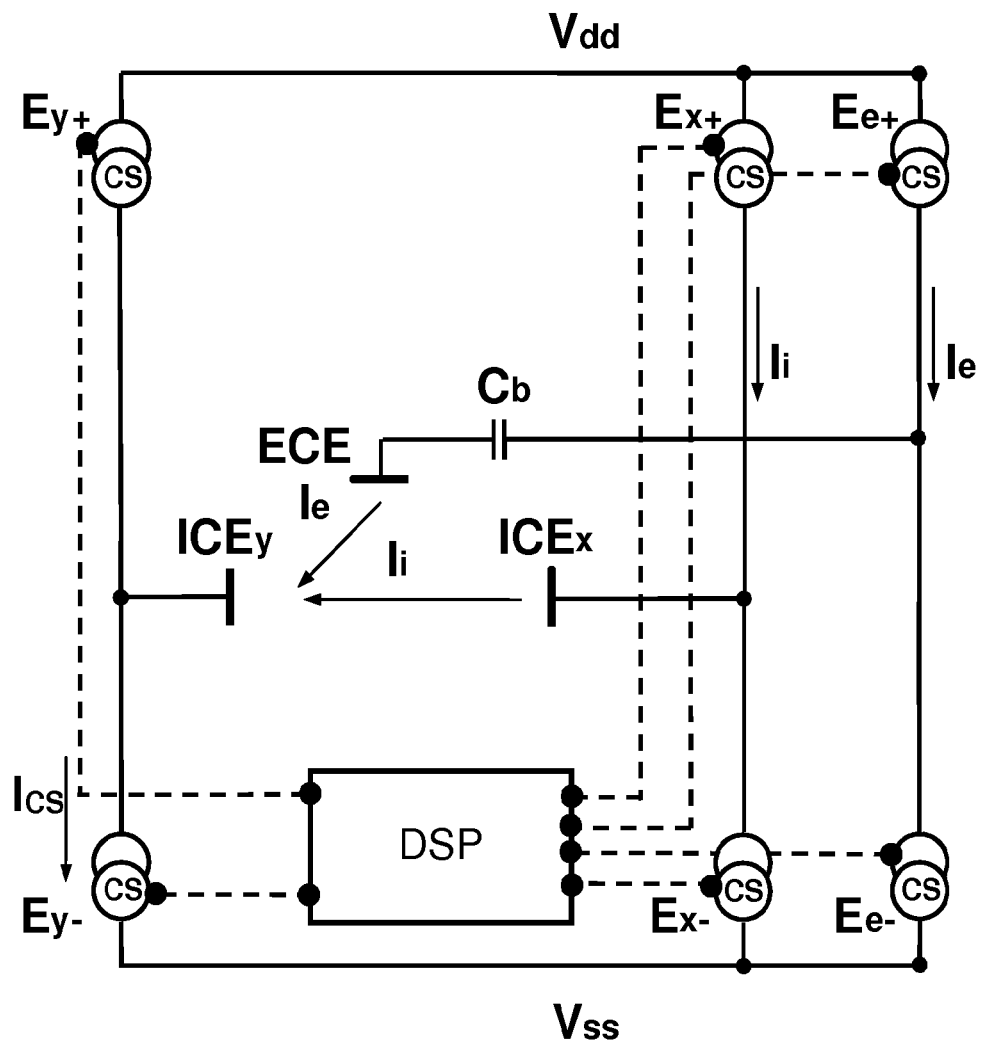
FIG. 11 illustrates a schematic circuit diagram of a third multiple current source embodiment during phase one of stimulation.

A further embodiment, as shown in FIG. 11, provides the same effect but without the need for a variable resistance circuit. FIG. 11 has the same components as FIG. 9a except for the absence of any variable resistance circuitry or switching circuitry and the addition of, a current control circuit, which in this case is a Digital Signal Processor DSP.

Although a Digital Signal Processor is used as the current control circuit in this example, any appropriate microprocessor capable of outputting a control signal, which, if required, can be converted from a digital to an analogue signal, capable of controlling the output of a current source. For example, the current source could be a Howland current source controlled by an input voltage which is directly related to the constant current. Notably, an input voltage of zero would, in an ideal current source, imply an open circuit. In an actual circuit, this can be sufficient to provide a substitute for a switch.

Components which are in both FIG. 9a and FIG. 11 are referenced in FIG. 11 with like references. The current sources CS are controlled accurately by the digital signal processing circuit DSP. In this case, the DSP can include digital to analogue converters to supply analogue control signals to the current sources CS. By controlling the current sources in this way, the total stimulation current can be proportionally divided between the extra-cochlear and intra-cochlear stimulation circuits in the digital signal processing circuit which in turn controls the output of the current sources. This removes the need for a variable resistance and simplifies the stimulation circuit.

Figure 12:
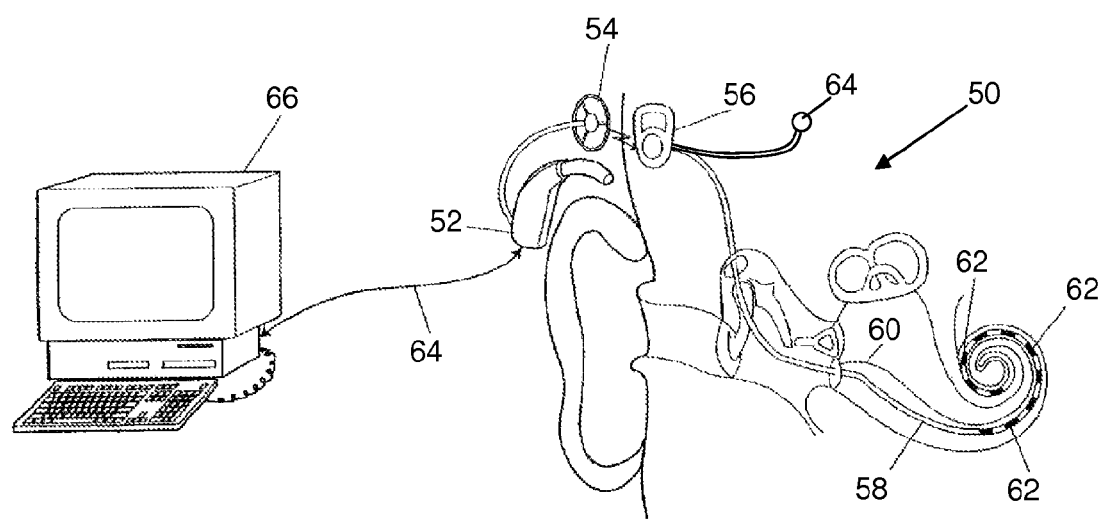
FIG. 12 illustrates a perspective view of an exemplary cochlear implant and a computer connected via a bi-directional communication link, in which embodiments of the present invention may be implemented.

Referring now to FIG. 12, a cochlear implant system 50, which is a type of implantable hearing device, is shown having an external module or speech processor 52, transmit antenna transmit antenna 54, receiver stimulator 56 and electrode array 58. The receiver stimulator 56 and electrode array 58 are implanted in the recipient with electrode array 58 placed within the cochlea 60. The electrode array 58 has plurality of electrodes 62, known as intra-cochlear electrodes, and at least one reference or extra-cochlear electrode 64. The speech processor 52 is in communication with the implanted portion of the cochlear implant system by means of an inductive link established between transmit antenna 54 and the receive antenna of the receiver stimulator 56. Processor 52 includes non-volatile memory which holds several different speech processing and stimulation strategy programs. The receiver stimulator 56 contains circuitry, as described above, to control current delivered to the stimulating electrodes, being the extra-cochlear electrode 64 or intra-cochlear electrodes 62, as required by the processor 52. In this manner, sound received by the processor 52 is processed into stimulation signals which the receiver stimulator 56 interprets and generations stimulation circuits between one or more electrodes 62, 64.

As previously mentioned with reference to FIG. 4, a clinician can set the ratio of intra-cochlear and extra-cochlear stimulation using a software tool. A computer 64 communicates using a bi-directional communication link 66. The software program as described with reference to FIG. 4 communicates a ratio of stimulation current which should be used which is stored in the memory of processor 52 and used for future stimulation of the recipient's cochlea.

As outlined above, it is particularly desirable to be able to provide simultaneous simulation of intra-cochlear electrodes and extra-cochlear electrodes so that auditory performance can be managed alongside power consumption. Simultaneous simulation in this manner has the benefit that it reduces extra-cochlear current flow compared to purely intra-cochlear stimulation. Therefore, simultaneous simulation of intra-cochlear and extra-cochlear electrodes can mitigate facial nerve stimulation, which can occur with some recipients with purely extra-cochlear stimulation.

It is noted that US 2005/0203590 specifically describes the arrangement of an electrode array in relation to prior art document U.S. Pat. No. 6,600,955. U.S. Pat. No. 6,600,955 uses a "floating" current source for each electrode and it is not possible to configure floating current sources to provide monopolar stimulation to more than one intra-cochlear electrode (since to do so the multiple current sources must be simultaneously connected to the same extra-cochlear electrode which renders them no longer floating). The "low power" configuration of US 2005/0203590 only considers low power with respect to monopolar stimulation. That is, simultaneous monopolar stimulation to two electrodes in the electrode array can provide lower power consumption than monopolar stimulation to a single electrode in the electrode array.

The simultaneous simulation method and circuit described herein considers both the stimulation performance advantages, such as auditory performance in an implantable hearing device, of bipolar stimulation alongside the power consumption advantages of monopolar stimulation. That is, it does reduce power below that of using only monopolar stimulation but does reduce power from purely bipolar stimulation, whilst still providing some benefits of bipolar stimulation.

It will be appreciated that many alternative implementations of the present invention are envisaged.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

The invention claimed is:

1. An implantable stimulator device including:
   at least one extra-cochlear electrode;
   an array of intra-cochlear electrodes;
   at least one current source; and
   at least one current control circuit configured to control the at least one current source to supply a first pre-defined proportion of a stimulation current to an extra-cochlear stimulation circuit between the at least one extra-cochlear electrode and one or more first intra-cochlear electrodes in the array, and to supply a second pre-defined proportion of the stimulation current to an intra-cochlear stimulation circuit between one or more second intra-cochlear electrodes in the array and the one or more first intra-cochlear electrodes.

2. The implantable stimulator device of claim 1, wherein the at least one current control circuit is operable to deliver biphasic stimulation, having a first phase in one polarity and a second phase in an opposite polarity, to the extra-cochlear stimulation circuit and the intra-cochlear stimulation circuit.

3. The implantable stimulator device of claim 1, wherein at least one current control circuit is configured to deliver triphasic stimulation having a first phase with the extra-cochlear stimulation circuit and the intra-cochlear stimulation circuit in one polarity, a second phase with the extra-cochlear stimulation circuit in the same polarity as in the first phase and the intra-cochlear stimulation circuit in the opposite polarity, and a third phase with the extra-cochlear stimulation circuit and the intra-cochlear stimulation circuit each in the opposite polarity as in the first phase.

4. The implantable stimulator device of claim 1, wherein the at least one current control circuit comprises a microprocessor capable of providing control signals to the at least one current source.

5. The implantable stimulator device of claim 1, wherein the at least one current control circuit comprises resistive circuitry.

6. The implantable stimulator device of claim 5, wherein the resistive circuitry is variable resistive circuitry.

7. The implantable stimulator device of claim 5, further comprising a plurality of switches between: a voltage supply and the at least one extra-cochlear electrode; a positive voltage supply and the array of intra-cochlear electrodes; a negative voltage supply and the at least one extra-cochlear electrode; and a negative voltage supply and the array of intra-cochlear electrodes, the switches configured to enable biphasic stimulation between the at least one extra-cochlear electrode and at least one of the intra-cochlear electrodes, and between at least one of the intra-cochlear electrodes and at least one other of the intra-cochlear electrodes.

8. The implantable stimulator device of claim 1, further comprising a feedback circuit, the feedback circuit configured to measure, directly or indirectly, the proportion of the stimulation current in the extra-cochlear stimulation circuit and the proportion of the stimulation current in the intra-cochlear stimulation circuit and provide the measurement to the control circuit, the control circuit configured to adjust the proportions of stimulation current based on the measurement.

9. The implantable stimulator device of claim 1, wherein the at least one current source is a single current source.

10. The implantable stimulator device of claim 1, wherein the implantable stimulator device is an implantable hearing device.

11. An implantable vestibular device comprising the implantable stimulator device of claim 1.

12. A method for providing electrical stimulation in an implant, the implant including at least one extra-cochlear electrode, an array of intra-cochlear electrodes, at least one current source, and at least one current control circuit, the method comprising:
controlling the at least one current source to deliver a first pre-defined proportion of a stimulation current to an extra-cochlear stimulation circuit between the at least one extra-cochlear electrode and one or more first intra-cochlear electrodes of the array; and
controlling the at least one current source to deliver a second pre-defined proportion of a stimulation current to an intra-cochlear stimulation circuit between one or more second intra-cochlear electrodes of the electrode array and the one or more first intra-cochlear electrodes.

13. The method of claim 12, further comprising measuring the proportion of the stimulation current in the extra-cochlear stimulation circuit and the proportion of the stimulation current in the intra-cochlear stimulation circuit.

14. The method of claim 13, further comprising providing the measurements to the control circuit.

15. The method of claim 14, further comprising adjusting the proportions of stimulation based on the measurements.

16. The method of claim 12, wherein the current control circuit comprises variable resistive circuitry to control the at least one current source.

17. The method of claim 15, wherein the current control circuit comprises variable resistive circuitry and wherein adjusting the proportions of stimulation comprises adjusting the variable resistive circuitry.

18. The method of claim 12, further comprising delivering biphasic stimulation, having a first phase in one polarity and a second phase in an opposite polarity, to the extra-cochlear stimulation circuit and the intra-cochlear stimulation circuit.

19. The method of claim 12, further comprising the current source delivering the first pre-defined proportion of the stimulation current and the second pre-defined proportion of the stimulation current simultaneously.

20. The implantable stimulator device of claim 1, wherein the extra-cochlear stimulation circuit includes the at least one extra-cochlear electrode, the one or more first intra-cochlear electrodes in the array and a conductor in between the at least one extra-cochlear electrode and the one or more first intra-cochlear electrodes in the array, and wherein the intra-cochlear stimulation circuit comprises the one or more second intra-cochlear electrodes in the array, the one or more first intra-cochlear electrodes and a conductor in between the one or more second intra-cochlear electrodes in the array and the one or more first intra-cochlear electrodes.

* * * * *

UNITED STATES PATENT AND TRADEMARK OFFICE
CERTIFICATE OF CORRECTION

| | | |
|---|---|---|
| PATENT NO. | : 8,644,944 B2 | Page 1 of 1 |
| APPLICATION NO. | : 13/388937 | |
| DATED | : February 4, 2014 | |
| INVENTOR(S) | : Edmond Capcelea et al. | |

It is certified that error appears in the above-identified patent and that said Letters Patent is hereby corrected as shown below:

In the drawings

In FIG. 3, replace the word "bipolar" with --monopolar--.

In FIG. 3, replace the word "monopolar" with --bipolar--.

In the specification

In column 4, line 45, replace the word "left" with --right--.

In column 4, line 46, replace the word "right" with --left--.

Signed and Sealed this
Second Day of August, 2016

Michelle K. Lee
*Director of the United States Patent and Trademark Office*